United States Patent
Schnabel et al.

(10) Patent No.: US 6,410,482 B1
(45) Date of Patent: *Jun. 25, 2002

(54) (HET) ARYLSULFONYLUREAS HAVING AN AMINO FUNCTION, THEIR PRESENTATION AND THEIR USE AS HERBICIDES AND PLANT GROWTH REGULATORS

(75) Inventors: Gerhard Schnabel, Grosswallstadt; Lothar Willms, Hofheim; Klaus Bauer, Hanau; Hermann Bieringer, Eppstein; Christopher Rosinger, Hofheim, all of (DE)

(73) Assignee: Hoechst Schering AgrEvo GmbH, Berlin (DE)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/855,251

(22) Filed: May 13, 1997

(30) Foreign Application Priority Data

May 15, 1996 (DE) .......................... 196 19 628

(51) Int. Cl.$^7$ .................... C07D 401/12; C07D 403/12; A01N 43/54

(52) U.S. Cl. ................ 504/214; 504/215; 544/320; 544/321; 544/323; 544/324; 544/331; 544/332; 544/58.5; 544/54; 544/63; 544/66; 544/96; 544/122; 544/123; 544/296; 540/601

(58) Field of Search ................ 504/214, 215; 544/320, 321, 323, 324, 331, 332, 58.5, 54, 63, 66, 96, 122, 123, 296

(56) References Cited

U.S. PATENT DOCUMENTS

| 4,225,337 A | 9/1980 | Levitt .......................... 544/321 |
|---|---|---|
| 4,369,058 A | 1/1983 | Levitt .......................... 544/323 |
| 4,453,971 A | 6/1984 | Levitt .......................... 544/211 |
| 4,664,695 A * | 5/1987 | Schurter et al. ............ 544/323 |
| 4,885,337 A | 12/1989 | Eichenauer et al. .......... 525/75 |
| 4,892,946 A | 1/1990 | Levitt .......................... 544/322 |

FOREIGN PATENT DOCUMENTS

| DE | 42 30 933 A1 | 3/1994 |
|---|---|---|
| EP | 0 116 518 | 8/1984 |

* cited by examiner

*Primary Examiner*—John M. Ford
(74) *Attorney, Agent, or Firm*—Frommer Lawrence & Haug LLP

(57) ABSTRACT

(Het)Arylsulfonylureas having an imino function, their preparation, and their use as herbicides and plant growth regulators Compounds of the formula (I) and salts thereof

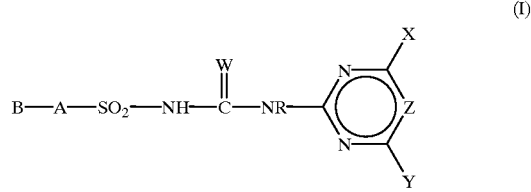

in which A is a (hetero)aromatic or heterocyclic bridge linked to the group SO$_2$ by a direct bond, or via O, S, NH, CH$_2$ or via alkylated NH or alkylated methylene, B is a group having an imino-containing fragment N=C—N, N=C—S, N=C—O or N=C—C which is linked to A by one of the nitrogen atoms of the fragment, R=H or an aliphatic radical, W=O or S and X, Y and Z are as defined in claim 1 are suitable as herbicides and plant growth regulators. The preparation is carried out for example similarly to known processes via novel intermediates of the formula (XII) (cf. claims 6 and 10),

8 Claims, No Drawings

(HET) ARYLSULFONYLUREAS HAVING AN AMINO FUNCTION, THEIR PRESENTATION AND THEIR USE AS HERBICIDES AND PLANT GROWTH REGULATORS

DESCRIPTION

The invention relates to the technical field of herbicides and plant growth regulators, in particular of herbicides for controlling broad-leaved weeds and grass weeds in crop plants.

N-Pyrimidinyl- or N-triazinyl(het)arylsulfonylureas carrying one or more certain substituents in the aromatic or heteroaromatic moiety are known to have herbicidal properties.

For example, phenylsulfonylureas having a nitrogen function with a certain substitution pattern (such as acylamino- or N-acyl-N-alkylamino) are potent herbicides; cf. for example DE-A4230933, EP-A-116 518, U.S. Pat. No. 4,885, 337, U.S. Pat. No. 4,892,946, U.S. Pat. No. 4,53,971, U.S. Pat. No. 4,369,058.

Surprisingly, it has now been found that sulfonylureas having specific nitrogen radicals are particularly suitable for use as herbicides and plant growth regulators.

The present invention provides compounds of the formula (I) or salts thereof,

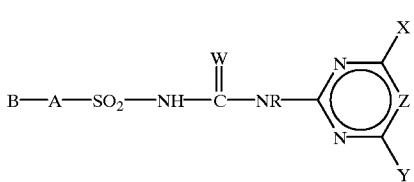

in which
A is an aromatic or heterocyclic divalent bridge, for example a carbocyclic aromatic or a saturated or unsaturated heterocyclic or heteroaromatic bridge, which is unsubstituted or substituted and linked to the $SO_2$ group in the respective compound of the formula (I) by a direct bond or via a group of the formula O, S, NH or $CH_2$, where NH or $CH_2$ are optionally substituted by $C_1$–$C_6$-alkyl radicals, B is a group which contains an imino-containing 3 atom fragment from the group of the fragments of the formulae N=C—N, N=C—S, N=C—O and N=C—C and which is attached to the radical A via a nitrogen atom of the fragment, R is H or an aliphatic radical, W is an oxygen or sulfur atom, X and Y are each independently of the other hydrogen, halogen, $C_1$–$C_6$-alkyl, $C_1$–$C_6$-alkoxy, $C_3$–$C_6$-alkylthio, $C_3$–$C_6$-cycloalkyl, $C_3$–$C_6$-cycloalkoxy, $C_3$–$C_6$-cycloalkylthio, $C_2$–$C_6$-alkenyl, $C_5$–$C_6$-cycloalkenyl, $C_2$–$C_6$-alkynyl, $C_3$–$C_6$-alkenyloxy, $C_5$–$C_6$-cycloalkenyloxy or $C_3$–$C_6$-alkynyloxy, each of the last eleven radicals being unsubstituted or substituted by one or more radicals from the group consisting of halogen, $C_1$–$C_4$-alkoxy, $C_1$–$C_4$-alkylthio, $C_1$–$C_4$-haloalkoxy and, in the case of cyclic radicals, also $C_1$–$C_4$-alkyl and $C_1$–$C_4$-haloalkyl, or are mono- or di-($C_1$–$C_4$-alkyl)amino and Z is CH or N.

In formula (I) and all subsequent formulae, the radicals alkyl, alkoxy, haloalkyl, haloalkoxy, alkylamino and alkylthio and the corresponding unsaturated and/or substituted radicals can be in each case straight-chain or branched in the carbon skeleton. Unless specifically indicated, the lower carbon skeletons, for example those having 1 to 4 carbon atoms or, in the case of unsaturated groups, 2 to 4 carbon atoms, are preferred for these radicals. Alkyl radicals, also in the composite meanings such as alkoxy, haloalkyl and the like, are, for example, methyl, ethyl, n-or i-propyl, n-, i-, t- or 2-butyl, pentyls, hexyls, such as n-hexyl, i-hexyl and 1,3-dimethylbutyl, heptyls, such as n-heptyls, 1-methylhexyl and 1,4-dimethylpentyl. Cycloalkyl is a cycloaliphatic hydrocarbon radical, such as cyclopropyl, cyclobutyl, cyclopentyl or cyclohexyl and the like; alkenyl, cycloalkenyl and alkynyl radicals have the meanings of the unsaturated radicals which are possible and which correspond to the alkyl radicals; alkenyl is, for example, allyl, 1-methylprop-2-en-1-yl, 2-methylprop-2-en-1-yl, but-2-en-1-yl, but-3-en-1-yl, 1-methylbut-3-en-1-yl and 1-methylbut-2-en-1-yl; cycloalkenyl is, for example, cyclopentenyl and cyclohexenyl; alkynyl is, for example, propargyl, but-2-yn-1-yl, but-3-yn-1-yl, 1-methylbut-3-yn-1-yl, Alkenyl in the form of "($C_3$–$C_4$)alkenyl" or "($C_3$–$C_6$) alkenyl" is preferably an alkenyl radical having 3 to 4 or 3 to 6 carbon atoms in which the double bond is not positioned at the carbon atom attached to the remainder of the molecule of the compound (I) ("y1" position). The same applies analogously to ($C_3$–$C_4$)-alkynyl, etc.

Halogen is, for example, fluorine, chlorine, bromine or iodine. Haloalkyl, -alkenyl and -alkynyl are alkyl, alkenyl and alkynyl, respectively, which are partially or fully substituted by halogen, preferably by fluorine, chlorine and/or bromine, in particular by fluorine or chlorine, for example $CF_3$, $CHF_2$, $CH_2F$, $CF_3CF_2$, $CH_2FCHCl$, $CCl_3$, $CHCl_2$, $CH_2CH_2Cl$; haloalkyl is, for example, $OCF_3$, $OCHF_2$, $OCH_2F$, $CF_3CF_2O$, $OCH_2CF_3$ and $OCH_2CH_2Cl$; the same applies analogously to haloalkenyl and other halogen-substituted radicals.

A hydrocarbon radical is a straight-chain, branched or cyclic, saturated or unsaturated, aliphatic or aromatic hydrocarbon radical, for example alkyl, alkenyl, alkynyl, cycloalkyl, cycloalkenyl or aryl; preferably alkyl, alkenyl or alkynyl having up to 12 carbon atoms or cycloalkyl having 3 to 8 ring atoms, preferably 5 or 6 ring atoms, or phenyl; the same applies analogously to a hydrocarbonoxy radical.

An organic radical is a carbon-containing radical having one or more optionally substituted aliphatic and/or (hetero) aromatic radicals. An aliphatic radical is a non-aromatic organic radical which may, in addition to carbon atoms and hydrogen atoms, also contain hetero atoms, preferably a non-aromatic hydrocarbon radical which is unsubstituted or substituted by one or more radicals from the group consisting of halogen, $C_1$–$C_4$-alkoxy and $C_1$–$C_4$-alkylthio.

Aryl is a mono-, bi- or polycyclic aromatic system, for example phenyl, naphthyl, tetrahydronaphthyl, indenyl; indanyl, pentalenyl, fluorenyl and the like, preferably phenyl; aryloxy is preferably an oxy radical corresponding to the aryl radical mentioned, in particular phenoxy.

Hetaryl or a heteroaromatic radical is a mono-, bi- or polycyclic aromatic system in which at least 1 ring contains one or more hetero atoms, for example pyridyl, pyrimidinyl, pyridazinyl, pyrazinyl, thienyl, thiazolyl, oxazoyl, furyl, pyrrolyl, pyrazolyl and imidazolyl. If substituted, this in particular also includes bicyclic or polycyclic aromatic compounds or compounds fused with cycloaliphatic rings, for example quinolinyl, benzoxazolyl, etc. Hetaryl also includes a heteroaromatic ring which is preferably 5- or 6-membered and contains 1, 2 or 3 hetero ring atoms, in particular from the group consisting of N, O and S. If substituted, the heteroaromatic ring may also be benzo-fused.

A heterocyclic radical (heterocyclyl) or ring (heterocycle) may be saturated, unsaturated or heteroaromatic; it preferably contains one or more hetero ring atoms, preferably selected from the group consisting of N, O and S; it is preferably a non-aromatic ring having 3 to 8 ring atoms and 1 to 3 hetero ring atoms from the group consisting of N, O and S, or it is a heteroaromatic ring having 5 or 6 ring atoms and contains 1, 2 or 3 hetero ring atoms from the group consisting of N, O and S. For example, the radical may be a heteroaromatic radical or ring as defined above, or it is a partially hydrogenated radical such as oxiranyl, pyrrolidyl, piperidyl, piperazinyl, dioxolanyl, morpholinyl, tetrahydro-furyl. Suitable substituents for a substituted heterocyclic radical are the substituents mentioned further below, and additionally also oxo. The oxo group may also be located on the hetero ring atoms which can exist at various oxidation levels, for example in the case of N and S.

Substituted radicals, such as substituted hydrocarbon radicals, for example substituted alkyl, alkenyl, alkynyl, aryl, phenyl and benzyl, or substituted hetaryl a substituted bicyclic radical or ring, or a substituted bicyclic radical, if appropriate with aromatic moieties, are, for example, a substituted radical which is derived from the unsubstituted skeleton, the substituents being, for example, one or more, preferably 1, 2 or 3, radicals selected from the group consisting of halogen, alkoxy, haloalkoxy, alkylthio, hydroxyl, amino, nitro, cyano, azido, alkoxycarbonyl, alkylcarbonyl, formyl, carbamoyl, mono- and dialkylaminocarbonyl, substituted amino, such as acylamino, mono- or dialkylamino, and alkylsulfinyl, haloalkylsulfinyl, alkylsulfonyl, haloalkylsulfonyl and, in the case of cyclic radicals, also alkyl and haloalkyl: and unsaturated aliphatic radicals, such as alkenyl, alkynyl, alkenyloxy, alkynyloxy and the like, corresponding to the abovementioned saturated hydrocarbon-containing radicals. Amongst radicals having carbon atoms, those having 1 to 4 carbon atoms, in particular 1 or 2 carbon atoms, are preferred. Preferred substituents are, as a rule, selected from the group consisting of halogen, for example fluorine and chlorine, $C_1$–$C_4$-alkyl, preferably methyl or ethyl, $C_1$–$C_4$-haloalkyl, preferably trifluoromethyl, $C_1$–$C_4$-alkoxy, preferably methoxy or ethoxy, $C_1$–$C_4$- haloalkoxy, nitro and cyano. Especially preferred in this context are the substituents methyl, methoxy and chlorine.

Optionally substituted phenyl is preferably phenyl which is unsubstituted or mono- or polysubstituted, preferably up to trisubstituted, by identical or different radicals selected from the group consisting of halogen, $C_1$–$C_4$-alkyl, $C_1$–$C_4$-alkoxy, $C_1$–$C_4$-haloalkyl, $C_1$–$C_4$-haloalkoxy and nitro, for example o-, m- and p-tolyl, dimethylphenyls, 2-, 3- and 4-chlorophenyl, 2-, 3- and 4-trifluoro- and -trichlorophenyl, 2,4-, 3,5-, 2,5- and 2,3-dichlorophenyl, o-, m- and p-methoxyphenyl.

Mono- or disubstituted amino is a chemically stable radical selected from the group consisting of the substituted amino radicals which are N-substituted, for example, by one or two identical or different radicals selected from the group consisting of alkyl, alkoxy, acyl and aryl; preferably monoalkylamino, dialkylamino, acylamino, arylamino, N-alkyl-N-arylamino and N-heterocycles; preferred in this context are alkyl radicals having 1 to 4 carbon atoms; aryl is, in this context, preferably phenyl or substituted phenyl; acyl is as defined further below, preferably $C_1$–$C_4$-alkanoyl. The same applies analogously to substituted hydroxylamino or hydrazino.

The invention also relates to all stereoisomers which are embraced by formula (I) and to their mixtures. Such compounds of the formula (I) contain one or more asymmetric carbon atoms or else double bonds which are not separately indicated in formula (I). The stereoisomers which are possible and which are defined by their specific spatial form, such as enantiomers, diastereomers and Z and E isomers, are all embraced by formula (I) and can be obtained from mixtures of the stereoisomers by customary methods, or else prepared by stereoselective reactions in combination with the use of stereochemically pure starting materials.

The formula (I) also includes tautomers of the compounds defined, insofar as they are formed by proton migration and insofar as they are chemically stable tautomers.

The compounds of the formula (I) can form salts where the hydrogen of the —$SO_2$—NH— group or else other acidic hydrogen atoms (for example from COOH and the like) are replaced by an agriculturally useful cation. These salts are, for example, metal salts; preferably alkali metal salts or alkaline earth metal salts, in particular sodium salts and potassium salts, or else ammonium salts or salts with organic amines. Salt formation can also be carried out by addition of an acid to basic groups, such as amino and alkylamino. Suitable acids in this context are strong inorganic and organic acids, for example HCl, HBr, $H_2SO_4$ or $HNO_3$.

Compounds of the formula (I) or salts thereof according to the invention which are of particular interest because of more potent herbicidal activity, better selectivity and/or because they can be prepared more easily, are those in which A is an aromatic or heteroaromatic bridge from the group consisting of phenyl, naphthyl and a heteroaromatic ring having 5 or 6 ring atoms and 1 or 2 hetero ring atoms from the group consisting of N, O and S which may also be benzo-fused, the bridge being unsubstituted or substituted and linked to the $SO_2$ group in the compound of the formula (1) by a direct bond or via a group of the formula O, S, NH, ($C_1$–$C_4$-alkyl)N or $CH_2$, B is an imino-containing group of the formula

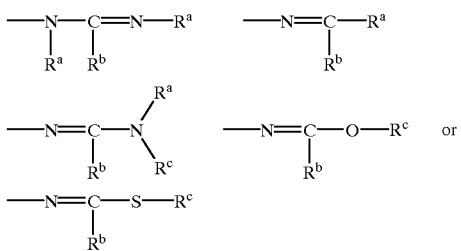

where the radicals $R^a$ are each independently of one another hydrogen, $NH_2$, OH or an aliphatic, aromatic, heterocyclic or another organic radical having a total of 1 to 12 carbon atoms which may also be attached via a hetero atom, the radicals $R^b$ are each independently of one another one of the radicals possible for $R^a$, excluding OH, the radicals $R^c$ are each independently of one another H or an aliphatic, aromatic, heterocyclic or another organic radical having a total of 1 to 20 carbon atoms, and where the radicals $R^a$ to $R^c$ may be paired to form a bridge in a group B, preferably an aliphatic bridge, the organic group B having a total of 1 to 30 carbon atoms, R is H or a hydrocarbon radical having 1 to 8 carbon atoms which is unsubstituted or substituted by one or more radicals from the group consisting of halogen, $C_1$–$C_4$-alkoxy and $C_1$–$C_4$-alkylthio, W is O or S, preferably O, one of the radicals X and Y is halogen, $C_1$–$C_6$-alkyl, $C_1$–$C_6$-alkoxy, $C_1$–$C_6$-alkylthio, the last 3 radicals being unsubstituted or substituted by one or more radicals from the group consisting of halogen, $C_1$–$C_4$-alkoxy and $C_1$–$C_4$-alkylthio, or is $C_2$–$C_4$-alkenyl, $C_2$–$C_4$-alkynyl, $C_2$–$C_4$-alkenyloxy or $C_2$–$C_4$-alkynyloxy, each of the last 4 radicals being unsubstituted or substituted by one or more halogen atoms, or is $C_3$–$C_6$-cycloalkyl or mono- or di-($C_1$–$C_2$-alkyl) amino and the other of the radicals X and Y is halogen, $C_1$–$C_4$-alkyl, $C_1$–$C_4$-alkoxy or $C_1$–$C_4$-alkylthio, each of the last 3 radicals being unsubstituted or substituted by one or more radicals from the group consisting of halogen, $C_1$–$C_4$-alkoxy and $C_1$–$C_4$-alkylthio, or is mono- or di-($C_1$–$C_2$-alkyl)amino and Z is CH or N.

Of particular interest are the compounds of the formula (I) or salts thereof according to the invention where A is a bridge of the formulae $A_1$–$A_9$

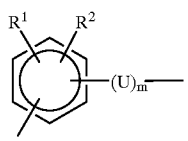
A₁

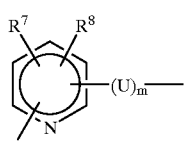
A₂

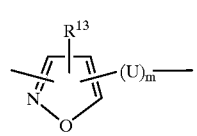
A₃

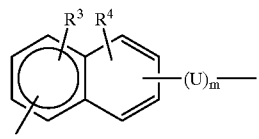
A₄

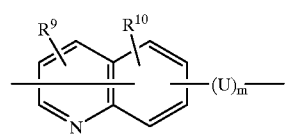
A₅

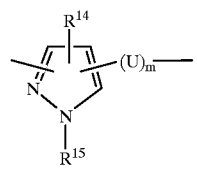
A₆

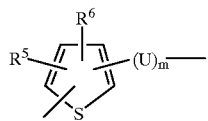
A₇

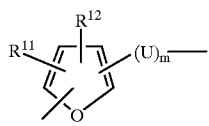
A₈

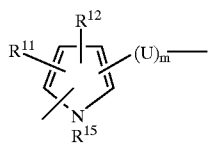
A₉

M is 0 or 1,
U is $CH_2$, O or NH or ($C_1$–$C_3$-alkyl)N,
B is a group of the formula B1 to B5,

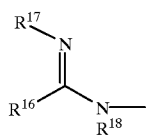
B1

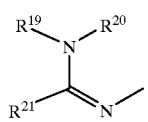
B2

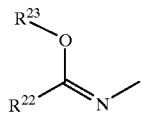
B3

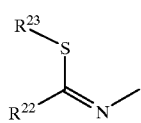
B4

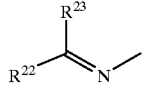
B5

R is hydrogen, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^1$ is H, CN, halogen, azide, $NO_2$, OH, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_1$–$C_8$-alkylsulfinyl, $C_2$–$C_8$-alkenylsulfinyl, $C_2$–$C_8$-alkynylsulfinyl, $C_1$–$C_8$-alkylsulfonyl, $C_2$–$C_8$-alkenylsulfonyl, $C_2$–$C_8$-alkynylsulfonyl, $C_3$–$C_8$-cycloalkyl, $C_3$–$C_8$-cycloalkyloxy, $C_3$–$C_8$-cycloalkylthio, $C_3$–$C_8$-cycloalkylsulfinyl, $C_3$–$C_8$-cycloalkylsulfonyl, $C_5$–$C_8$-cycloalkenyl, $C_5$–$C_8$-cycloalkenyloxy, $C_5$–$C_8$-cycloalkenylthio, $C_5$–$C_8$- cycloalkenylsulfinyl or $C_5$–$C_8$-cycloalkenylsulfonyl, each of the last 25 radicals being unsubstituted or substituted by one or more radicals from the group consisting of halogen, $C_1$–$C_4$-alkoxy, $C_1$–$C_4$-haloalkoxy, $C_1$–$C_4$-alkylthio, $C_1$–$C_4$-haloalkylthio, OH, CN, $NO_2$, oxo, $C_1$–$C_4$-alkylsulfonyl, $C_1$–$C_4$-haloalkylsulfonyl, ($C_1$–$C_4$-alkoxy)carbonyl, ($C_1$–$C_4$-haloalkoxy)-carbonyl, $NR^{32}R^{33}$ and, in the case of cyclic radicals, also $C_1$–$C_4$-alkyl and $C_1$–$C_4$-haloalkyl, or is $COR^{24}$, $CS$—$R^{25}$, $C(=NR^{26})R^{27}$, $NR^{28}R^{29}$, $SO_2NR^{30}R^{31}$ or a 3- to 7-membered heterocycle having up to 4 hetero atoms from the group consisting of N, O and S which is unsubstituted or substituted by one or more radicals from the group consisting of halogen, $C_1$–$C_4$-alkyl, OH, CN, $NO_2$, CHO, $NH_2$, mono- and di-($C_1$–$C_4$-alkyl)amino, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl and oxo, or is aryl, hetaryl, aryl-$C_1$–$C_3$-alkyl or hetaryl-$C_1$–$C_3$-alkyl, preferably phenyl or phenyl-$C_1$–$C_3$-alkyl, the aryl or hetaryl moiety of each of the last 6 radicals being unsubstituted or substituted by one or more radicals from the group consisting of halogen, OH, CN, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkylcarbonyl, $C_1$–$C_4$-haloalkylcarbonyl, ($C_1$–$C_4$-alkoxy)carbonyl, ($C_1$–$C_4$-haloalkoxy)carbonyl, mono- and di($C_1$–$C_4$-alkyl)amino, CHO, $NH_2$, $CONH_2$, mono- and di-($C_1$–$C_4$-alkyl)-aminocarbonyl, $R^2$ is hydrogen, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_1$–$C_8$-alkylsulfonyl, $C_2$–$C_8$-alkenylsulfonyl, $C_2$–$C_8$-alkynylsulfonyl, $C_3$–$C_8$-cycloalkyl, $C_5$–$C_8$-cycloalkenyl, $C_5$–$C_8$-cycloalkoxy, $C_5$–$C_8$-cycloalkenyloxy, $C_3$–$C_8$-cycloalkylthio, $C_5$–$C_8$-cycloalkenylthio, $C_3$–$C_8$-cycloalkylsulfonyl or $C_5$–$C_8$-cycloalkenylsulfonyl, each of the last 20 radicals being unsubstituted or substituted by one or more radicals from the group consisting of halogen, $C_1$–$C_4$-alkoxy and $C_1$–$C_4$-haloalkoxy and, in the case of cyclic radicals, also $C_1$–$C_4$-alkyl and $C_1$–$C_4$-haloalkyl, or is halogen, CN, $NH_2$, mono- or di-($C_1$–$C_4$-alkyl)amino, $R^3$, $R^5$, $R^7$, $R^9$, $R^{11}$, $R^{13}$ and $R^{14}$ are each a radical from the group of the radicals possible for $R^1$, $R^4$, $R^6$, $R^8$, $R^{10}$ and $R^{12}$ are each a radical from the group of the radicals possible for $R^2$, $R^{15}$ is hydrogen, $C_1$–$C_8$-alkyl, $C_3$–$C_8$-cycloalkyl, $C_1$–$C_8$-haloalkyl, $C_3$–$C_8$-halocycloalkyl, or aryl, in particular phenyl, which is unsubstituted or substituted by one or more radicals from the group consisting of halogen, $C_1$–$C_4$-alkyl, $C_1$–$C_4$-haloalkyl, $C_1$–$C_4$-alkoxy and $C_1$–$C_4$-haloalkoxy, $R^{16}$ is $NH_2$, hydrogen, aryl or hetaryl, in particular phenyl, the aryl, hetaryl or phenyl radical being unsubstituted or substituted, in particular unsubstituted or substituted by one or more radicals from the group consisting of halogen, $C_1$–$C_4$-alkyl, $C_1$–$C_4$-haloalkoxy, $C_1$–$C_4$-alkoxy, $C_1$–$C_4$-haloalkyl, CN and nitro, or is $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_3$–$C_8$-cycloalkyl, $C_5$–$C_8$-cycloalkenyl, $C_3$–$C_6$-cycloalkoxy, $C_5$–$C_8$-cycloalkenyloxy, $C_3$–$C_8$-cycloalkylthio, $C_5$–$C_8$-cycloalkenylthio, mono- or di-($C_1$–$C_6$)alkylamino, each of the last 17 radicals being unsubstituted or substituted, in particular unsubstituted or substituted by one or more radicals from the group consisting of halogen, $C_1$–$C_4$-haloalkoxy, $C_1$–$C_4$-alkoxy, CN, oxo, ($C_1$–$C_4$-alkoxy)carbonyl and, in the case of cyclic radicals, also $C_1$–$C_4$-alkyl and $C_1$–$C_4$-haloalkyl, or is benzyl, CN, ($C_1$–$C_6$-alkoxy)carbonyl, ($C_1$–$C_6$-alkyl)carbonyl, benzyloxycarbonyl or phenylcarbonyl, $R^{17}$ is OH, $NH_2$, hydrogen, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, ($C_1$–$C_8$-alkyl)carbonyl, ($C_1$–$C_8$-alkoxy)carbonyl, benzoyl, benzyloxycarbonyl, ($C_1$–$C_8$)-alkylsulfonyl, arylsulfonyl, in particular phenylsulfonyl, $C_3$–$C_8$-cycloalkyl, $C_5$–$C_8$-cycloalkenyl, $C_3$–$C_8$-cycloalkoxy, $C_5$–$C_8$-cycloalkenyloxy, $C_3$–$C_8$-cycloalkylcarbonyl, $C_3$–$C_8$-cycloalkoxycarbonyl, $C_3$–$C_8$-cyclo-alkylsulfonyl, mono- or di-($C_1$–$C_8$-alkyl)amino, each of the last 22 radicals being unsubstituted or substituted by one or more radicals from the group consisting of halogen, $C_1$–$C_4$-alkoxy, $C_1$–$C_4$-haloalkoxy, CN, $NO_2$, OH, $NH_2$, mono- and di-($C_1$–$C_3$-alkyl)amino, $C_1$–$C_4$-alkylthio and $C_1$–$C_4$-haloalkylthio and, in the case of cyclic radicals, also $C_1$–$C_4$-alkyl and $C_1$–$C_4$-haloalkyl, or is aryl, in particular phenyl, or hetaryl, in particular furanyl or thienyl, each of the last 5 radicals being unsubstituted or substituted by one or more radicals from the group consisting of $C_1$–$C_4$-alkyl, $C_1$–$C_4$-haloalkyl, $C_1$–$C_4$-alkoxy, $C_1$–$C_4$-haloalkoxy, CN and $NO_2$, or the part of the formula

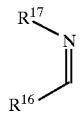

from the group of the abovementioned formula B1 (see definition of B) as a whole forms a heterocyclic ring having an imino function in the ring, preferably a heterocyclic ring having 5 or 6 ring atoms and, in addition to the nitrogen atom of the imino group, 1 or 2 hetero ring atoms from the group consisting of N, O and S, in particular a ring of the formulae D1 to D15

D1

D2

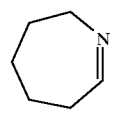

D3

 D4

 D5

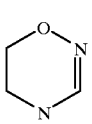 D6

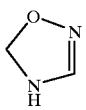 D7

 D8

 D9

 D10

 D11

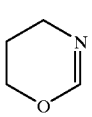 D12

 D13

 D14

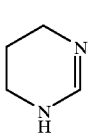 D15 the heterocyclic ring or each of the rings D1 to D15 being unsubstituted or substituted, preferably unsubstituted or substituted by one or more radicals from the group consisting of halogen, $C_1-C_4$-alkyl, $C_1-C_4$-haloalkyl, $C_1-C_4$-haloalkoxy, OH, $NH_2$, CN, $NO_2$, mono- and di-$(C_1-C_4$-alkyl)amino, $R^{18}$ is hydrogen, $C_1-C_8$-alkyl, $C_2-C_8$-alkenyl, $C_2-C_8$-alkynyl, $C_1-C_8$-alkylsulfonyl, $(C_1-C_8$-alkyl)carbonyl, $(C_1-C_8$-alkoxy)carbonyl, $C_1-C_8$-alkoxy, $C_3-C_8$-cycloalkyl, $C_5-C_8$-cycloalkenyl, $C_3-C_8$-cycloalkylsulfonyl, $C_3-C_8$-cycloalkylcarbonyl, $C_3-C_8$-cycloalkoxycarbonyl or $C_3-C_8$-cycloalkoxy, each of the last 13 radicals being unsubstituted or substituted by one or more radicals from the group consisting of halogen, $C_1-C_3$-alkoxy, $C_1-C_3$-haloalkoxy and, in the case of cyclic radicals, also $C_1-C_4$-alkyl and $C_1-C_4$-haloalkyl, or is CHO, $NH_2$, OH, mono- or di-$(C_1-C_4$-alkyl)amino, $R^{19}$ is a radical from the group of the radicals possible for $R^{17}$ and $R^{20}$ is hydrogen, $C_1-C_8$-alkyl, $C_3-C_8$-cycloalkyl, $C_5-C_8$-cycloalkenyl, $C_2-C_6$-alkenyl or $C_2-C_8$-alkynyl or $NR^{19}R^{20}$ is a heterocyclic ring, preferably having 3 to 6 ring atoms and, in addition to the 1-nitrogen atom, 0, 1 or 2 hetero ring atoms from the group consisting of N, O and S, in particular a functional group of the formulae E1 to E9,

E1

E2

E3

E4

E5

E6

E7

E8

E9 each of the heterocyclic radicals being unsubstituted or substituted by one or more radicals from the group consisting of halogen, $C_1-C_4$-alkyl, $C_1-C_4$-haloalkyl, $C_1-C_4$-alkoxy, $C_1-C_4$-haloalkoxy, OH, $NH_2$, $NO_2$, CN, mono- and di-$(C_1-C_5$-alkyl)amino, $R^{21}$ is a radical from the group of the radicals possible for $R^{16}$, $R^{22}$ is hydrogen, $C_1-C_8$-alkyl, $C_2-C_8$-alkenyl, $C_2-C_8$-alkynyl, $C_1-C_8$-alkoxy $C_1-C_8$-alkythio, $C_3-C_8$-cycloalkoxy, $C_3-C_8$-cycloalkylthio, $C_3-C_8$-cycloalkyl, $C_5-C_8$-cycloalkenyl, mono- or di-($C_1-C_8$-alkyl)amino, each of the last 11 radicals being unsubstituted or substituted by one or more radicals from the group consisting of CN, halogen, $C_1-C_4$-alkoxy, $C_1-C_4$-haloalkoxy and, in the case of cyclic radicals, also $C_1-C_4$-alkyl and $C_1-C_4$-haloalkyl, or is an aromatic or heteroaromatic monocycle or polycycle, preferably phenyl, thienyl, pyridyl, furanyl, each of these radicals being unsubstituted or substituted, preferably unsubstituted or substituted by one or more radicals from the group consisting of halogen, $C_1-C_4$-alkyl, $C_1-C_4$-haloalkyl, $C_1-C_4$-alkoxy, $C_1-C_4$-haloalkoxy, CN and nitro, $R^{23}$ is $C_1-C_8$-alkyl, $C_2-C_8$-alkenyl, $C_2-C_8$-alkynyl, $C_3-C_8$-cycloalkyl, $C_5C_8$-cycloalkenyl, heterocyclyl, aryl, in particular phenyl, or benzyl, each of the last 9 radicals being unsubstituted or substituted by one or more radicals from the group consisting of halogen, $C_1-C_4$-alkoxy, $C_1-C_4$-haloalkoxy, CN and $NO_2$ and, in the case of cyclic radicals, also $C_1-C_4$-alkyl and $C_1-C_4$-haloalkyl, $R^{24}$ is hydrogen, OH, $NH_2$, aryl or a heterocycle, preferably phenyl, furyl, thienyl or pyridyl, each of the last 6 radicals being unsubstituted or substituted, in particular unsubstituted or substituted by one or more radicals from the group consisting of halogen, $C_1-C_4$-alkyl, $C_1-C_4$-haloalkyl, CN, $NH_2$ and nitro, or is $C_1-C_8$-alkyl, $C_2-C_8$-alkenyl, $C_2-C_8$-alkynyl, $C_1-C_8$-alkoxy, $C_2-C_8$-alkenyloxy, $C_2-C_8$-alkynyloxy, $C_1-C_8$-alkylthio, $C_2-C_8$-alkenylthio, $C_2-C_8$-alkynylthio, benzyl or aryloxy, in particular phenoxy, or is benzyloxy, $C_3-C_8$-cycloalkyl, $C_5-C_8$-cycloalkenyl, $C_3-C_8$-cycloalkoxy, $C_5-C_8$-cycloalkenyloxy, $C_5-C_8$-cycloalkylthio or $C_5-C_8$-cycloalkenylthio, mono- or di-($C_1-C_8$-alkyl)amino, each of the last 21 radicals being unsubstituted or substituted by one or more radicals from the group consisting of halogen, $C_1-C_4$-alkoxy, $C_1-C_4$-haloalkoxy, OH, $NH_2$, mono- and di($C_1-C_4$-alkyl)amino, CN and $NO_2$ and, in the case of cyclic radicals, also $C_1-C_4$-alkyl and $C_1-C_4$-haloalkyl, $R^{25}$ is a radical from the group of the radicals possible for $R^{24}$, $R^{26}$ is hydrogen, OH, $NH_2$, CN, $C_1-C_8$-alkoxy, $C_2-C_8$-alkenyloxy, $C_2-C_8$-alkynyloxy, $C_1-C_8$-alkyl, $C_2-C_8$-alkenyl, $C_2-C_8$-alkynyl, $C_1-C_8$-alkylsulfonyl, $C_2-C_8$-alkenylsulfonyl, $C_2-C_8$-alkynylsulfonyl, $C_3-C_8$-cycloalkoxy, $C_5-C_8$-cycloalkenyloxy, $C_3-C_8$-cycloalkyl, $C_5-C_8$-cycloalkenyl, $C_3-C_8$-cycloalkylsulfonyl, $C_5-C_8$-cycloalkenylsulfonyl, arylsulfonyl, in particular phenylsulfonyl, or aryl or a heterocycle, in particular phenyl, furyl, thienyl or pyridyl, or benzyl, ($C_1-C_8$-alkoxy)carbonyl, ($C_1-C_8$-alkyl)carbonyl, phenoxycarbonyl, benzylcarbonyl or heterocyclylcarbonyl, in particular furylcarbonyl, pyridylcarbonyl or thienylcarbonyl, each of the last 32 radicals being unsubstituted or substituted, preferably unsubstituted or substituted by one or more radicals from the group consisting of halogen, $C_1-C_4$-alkoxy, $C_1-C_4$-haloalkoxy, oxo, CN, $C_1-C_4$-alkylthio, $C_1-C_4$-haloalkylthio, $C_1-C_4$-alkylsulfinyl, $C_1-C_4$-haloalkylsulfinyl, $C_1-C_4$-alkylsulfonyl, $C_1-C_4$-haloalkylsulfonyl and, in the case of cyclic radicals, also $C_1-C_4$-alkyl and $C_1-C_4$-haloalkyl, $R^{27}$ is a radical from the group of the radicals possible for $R^{24}$, excluding OH, $R^{28}$ is H, OH, CHO, $C_1-C_8$-alkyl, $C_2-C_8$-alkenyl, $C_2-C_8$-alkynyl, $C_1-C_8$-alkoxy, $C_2-C_8$-alkenyloxy, $C_2-C_8$-alkynyloxy, $C_1-C_8$-alkylsulfonyl, $C_2-C_8$-alkenylsulfonyl, $C_2-C_8$-alkynylsulfonyl, ($C_1-C_8$-alkyl)carbonyl, ($C_2-C_8$-alkenyl)carbonyl, ($C_2-C_8$-Alkynyl)-carbonyl, ($C_1-C_8$-alkoxy)carbonyl, ($C_2-C_8$-alkenyloxy)carbonyl, ($C_2-C_8$-alkynyloxy)carbonyl, mono- or di-($C_1-C_8$-alkyl)-aminocarbonyl, $C_3-C_8$-cycloalkyl, $C_5-C_8$-cycloalkenyl, $C_3-C_8$-cyloalkoxy, $C_5-C_8$-cycloalkenyloxy, $C_3-C_9$-cycloalkylsulfonyl, $C_5-C_8$-cycloalkenylsulfonyl, $C_3-C_8$-cycloalkoxycarbonyl, $C_5-C_8$-cycloalkenyloxycarbonyl, benzoyl, benzyl, benzylcarbonyl, benzyloxycarbonyl, aryl or a heterocycle, in particular phenyl, furyl, pyridyl or thienyl, each of the last 35 radicals being unsubstituted or substituted, preferably unsubstituted or substituted by one or more radicals from the group consisting of halogen, $NO_2$, CN, $C_1-C_4$-alkoxy, $C_1-C_4$-haloalkoxy, $C_1-C_4$-alkylthio, $C_1-C_4$-haloalkylthio, $NH_2$, $NH-CH_3$ and $N(CH_3)_2$ and, in the case of cyclic radicals, also $C_1-C_4$-alkyl and $C_1-C_4$-haloalkyl, or is $SO_2NH_2$ or $CONH_2$, $R^{29}$ is a radical from the group of the radicals possible for $R^{28}$, excluding OH, $R^{30}$ is a radical from the group of the radicals possible for $R^{19}$, $R^{31}$ is a radical from the group of the radicals possible for $R^{20}$, or $NR^{30}R^{31}$ as a whole forms a heterocyclic ring as defined for $NR^{19}R^{20}$, $R^{32}$ is hydrogen, $C_1-C_4$-alkyl, $C_1-C_4$-haloalkyl, CHO, $C_1-C_4$-alkylsulfonyl, $C_2-C_4$-alkenyl, $C_2-C_4$-alkynyl, $C_2-C_4$-haloalkenyl, $C_1-C_4$-haloalkyl, $C_2-C_4$-haloalkynyl, $C_1-C_4$-haloalkylsulfonyl, ($C_1-C_4$-alkyl)carbonyl, ($C_1-C_4$-alkoxy)carbonyl, ($C_1-C_4$-haloalkyl)carbonyl or ($C_1-C_4$-haloalkoxy)carbonyl, $R^{33}$ is a radical from the group of the radicals possible for $R^{32}$ or $NR^{32}R^{33}$ as a whole forms a heterocyclic ring as defined for $NR^{19}R^{20}$.

Of particular interest are also compounds of the formula (I) or salts thereof according to the invention where A is a radical of the already mentioned formula
$A_1$, in which m=0 or m=1 and $U=CH_2$, or
$A_2$, in which m=0, or
$A_6$, in which m=0, or
$A_7$, in which m=0, preferably a radical of the formula $A_1$ or $A_2$ already mentioned where in each case m=0.

Of particular interest are also compounds of the formula (I) (including salts thereof) according to the invention where B is a group of the formula B1, B2 or B3 already mentioned, in particular B2.

Preferred meanings of the individual radicals are listed below:

R=hydrogen, $C_2-C_3$-alkyl, $C_1-C_3$-alkoxy, preferably hydrogen or methyl;

$R^1$=H, CN, $NO_2$, halogen, $C_1-C_6$-alkoxy, $C_1-C_6$-alkyl, $C_1-C_6$-haloalkoxy, $C_1-C_6$-haloalkyl, ($C_1-C_6$-alkoxy)

carbonyl, ($C_3$–$C_6$-cycloalkoxy)carbonyl or ($C_3$–$C_6$-cycloalkyl)methoxycarbonyl, for example

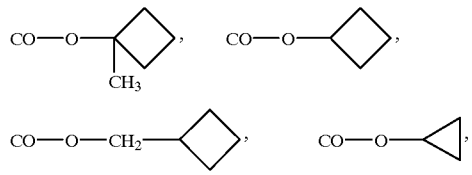

$COOCH_3$, $COOC_2H_5$ or $CO$—$O$—$CH(CH_3)_2$, or $C_1$–$C_6$-alkylthio, $C_1$–$C_6$-haloalkylthio, $C_1$–$C_6$-alkylsulfonyl, $C_1$–$C_6$-haloalkylsulfonyl, $SO_2NH_2$, $CONH_2$, mono- or di-($C_1$–$C_4$-alkyl)aminocarbonyl or -aminosulfonyl or a radical of the formula

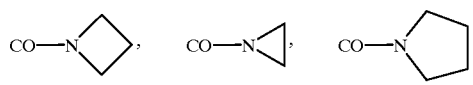

$C_1$–$C_6$-alkylcarbonyl, $C_1$–$C_6$-haloalkylcarbonyl, CHO, cyclopropylcarbonyl, cyclobutylcarbonyl or $NR^{28}R^{29}$;

$R^2$=hydrogen, $C_1$–$C_6$-alkyl, $C_1$–$C_6$-haloalkyl, $C_1$–$C_6$-alkoxy, $C_1$–$C_6$-haloalkoxy halogen or CN;

$R^3$, $R^5$, $R^7$, $R^9$, $R^{11}$, $R^{13}$ and $R^{14}$ are preferably defined as for the radicals preferred for $R^1$;

$R^4$, $R^6$, $R^8$, $R^{10}$, $R^{12}$ are preferably defined as for preferred $R^2$;

$R^{15}$=H, $C_1$–$C_3$-alkyl or phenyl;

$R^{16}$=H, $NH_2$, mono- or di-($C_1$–$C_6$-alkyl)amino, $C_1$–$C_6$-alkyl, phenyl, $C_1$–$C_6$-alkoxy, each of the last 5 radicals being unsubstituted or substituted by one or more radicals from the group consisting of halogen, $C_1$–$C_3$-alkoxy, $C_1$–$C_3$-haloalkoxy, CN, $NO_2$ and, in the case of phenyl, also $C_1$–$C_3$-alkyl and $C_1$–$C_3$-haloalkyl;

$R^{17}$=mono- or di-($C_1$–$C_6$-alkyl)amino, $C_1$–$C_6$-alkyl, $C_1$–$C_6$-alkoxy, phenyl, benzyl, each of the last 6 radicals being unsubstituted or substituted by one or more radicals from the group consisting of halogen, $C_1$–$C_3$-alkoxy, $C_1$–$C_3$-haloalkoxy and, in the case of phenyl, also $C_1$–$C_3$-alkyl and $C_1$–$C_3$-haloalkyl, or is OH, $NH_2$ or H;

or the part of the formula $R^{17}$—N=C—$R^{16}$ from the group of the formula B1 in the definition for B as a whole forms a heterocycle of the formula D1 or D2

D1

D2
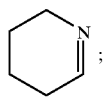

$R^{18}$=H, $C_1$–$C_6$-alkyl or $C_1$–$C_6$-haloalkyl, in particular H, $CH_3$, $C_2H_5$, $CF_3$ or $CH_2CF_3$, $R^{19}$=H, $C_1$–$C_6$-alkyl, $C_1$–$C_6$-haloalkyl, $C_1$–$C_6$-haloalkoxy or phenyl, $R^{20}$=H, $C_1$–$C_6$-alkyl, $C_1$–$C_6$-haloalkyl or phenyl or $NR^{19}R^{20}$ as a whole forms a heterocycle of the formula

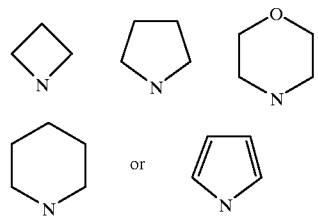

$R^{21}$=a radical from the group of the radicals preferred for $R^{16}$;

$R^{22}$=H, $C_1$–$C_6$-alkyl, $C_1$–$C_6$-haloalkyl or phenyl;

$R^{23}$=$C_1$–$C_6$-alkyl or $C_1$–$C_6$-haloalkyl;

$R^{28}$=H, $C_1$–$C_6$-alkyl, OH, $C_1$–$C_6$-haloalkyl, or $C_1$–$C_6$-alkoxy, $R^{29}$H, $C_1$–$C_6$-alkyl, $C_1$–$C_6$-haloalkyl, CHO, $C_1$–$C_3$-alkylsulfonyl, $C_1$–$C_3$-alkoxycarbonyl or $C_1$–$C_3$-alkylcarbonyl;

X and Y=Cl, F, $CF_3$, $CH_3$, $CH_2CH_3$, $OCH_3$, $OC_2H_5$, $N(CH_3)_2$, $NHCH_3$ or $OCH_2CF_3$.

The present invention also provides processes for preparing the compounds of the formula (I) or salts thereof according to the invention which comprise a) reacting a compound of the formula (II)

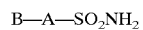
B—A—$SO_2NH_2$ (II)

with a heterocyclic carbamate of the formula (III)

(III)
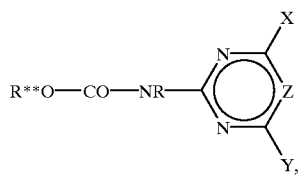

where R** is unsubstituted or substituted phenyl or $C_1$–$C_4$-alkyl, or b) reacting a sulfonyl isocyanate of the formula (IV)

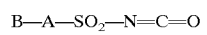
B—A—$SO_2$—N=C=O (IV)

with a heteroryclic amine of the formula (V)

(V)
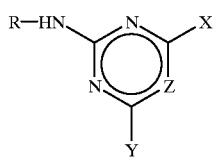

c) reacting a sulfonyl chloride of the formula (VI)

B—A—$SO_2Cl$ (VI)

with a heterocyclic amine of the formula (V) already mentioned in the presence of a cyanate, for example an alkali metal cyanate such as sodium cyanate or potassium cyanate, or d) reacting a sulfonyl chloride of the formula (II) already mentioned with a (thio)isocyanate of the formula (VII)

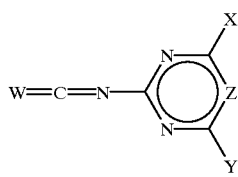
(VII)

in the presence of a suitable base, for example potassium carbonate or triethylamine, e) if B is a group containing a fragment of the formula —N=C—NR$^a$— where R$^a$ is NH$_2$, OH or an organic radical having 1 to 12 carbon atoms, reacting an amino-substituted sulfonylurea of the formula (VIII),

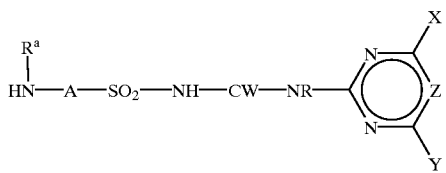
(VIII)

where R$^a$ is as defined above, with suitable reagents which contain a fragment of the formula (IXa)

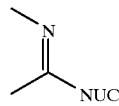
(IXa)

where NUC is a nucleofugal group (leaving group), for example Cl, f) if B is a group containing a fragment of the formula

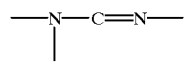

reacting an amino-substituted sulfonylurea of the formula (VIII) already mentioned (cf. e) where R$^a$=hydrogen with suitable reagents containing a fragment of the formula (Ixb)

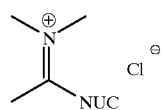
(IXb)

where NUC is a nucleofugal group (leaving group), for example Cl, where the radicals A, B, R, W, X, Y and Z in the formulae (II) to (IX) are as defined for the formula (I) and where the compounds initially obtained in variants a) to c) are compounds of the formula (I) where W is an oxygen atom.

The sulfonamides of the formula (II), the sulfonyl isocyanates of the formula (IV) and the sulfonyl chlorides of the formula (VI) are as novel compounds part of the subject matter of the invention.

The reaction of the compounds of the formulae (II) and (III) is preferably carried out under base catalysis in inert solvents, such as dichloromethane, acetonitrile, dioxane, dimethylformamide (DMF), dimethylacetamide or tetrahydrofuran (THF), at temperatures of from −10° C. to the boiling point of the respective solvent. Suitable bases are, for example, organic amine bases, such as 1,8-diazabicyclo [5.4.0]undec-7-ene (DBU), or triethylamine, or oxygen bases, such as hydroxides, for example sodium hydroxide or potassium hydroxide, or alkoxides, for example sodium methoxide, potassium tert-butoxide or sodium phenolate, or carbonates, for example sodium carbonate or potassium carbonate (cf. for example EP-A44807).

The sulfonamides of the formula (II) can be obtained for example from the compounds of the formula (X) by reacting the amino function with suitable reagents, for example compounds of the formula (IX), ortho esters or amide acetals, to give compounds of the formula B—A—SO$_2$NH—$^t$Bu (XI), and subsequent removal of the tert-butyl group from compounds of the formula (XI) with acids.

Examples of preferred intermediates of the formula (XI) and (II) are listed in Scheme 1 and Scheme 2, the radicals A and R$^{17}$ to R$^{23}$ being defined as further above; the compounds that have not been mentioned as examples can be prepared in a similar manner, if appropriate with the aid of additional customary methods.

Scheme 1: Preparation of the sulfonamides (II)

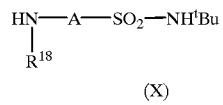
(X)

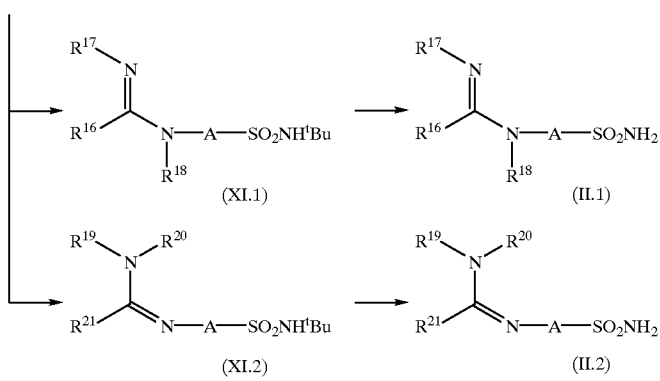

Scheme 2: Preparation of the sulfonamides (II)

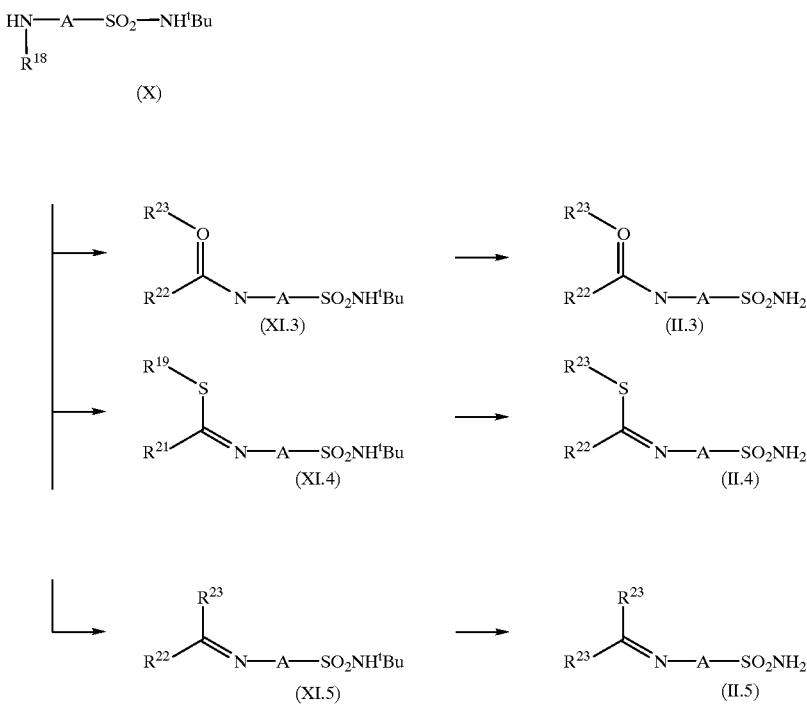

The compounds of the formula (XI) can be prepared by a number of standard reactions:

Compounds of the formula (XI. 1) can be obtained for example by reacting compounds of the type of the formula (IX.a) mentioned (Houben-Weyl-Falbe, "Methoden der organischen Chemie", 4th edition, volume E 5/1, p. 628 f) with sulfonamides of the formula (X)(Houben-Weyl-Falbe, "Methoden der organischen Chemie", 4th edition, volume E5/2, p. 1305ff).

If $R^{21}$ is hydrogen or a substituent attached via a carbon atom, the compounds of the formula (XI.2) can be prepared by reacting the sulfonamides (X) for example with salts of formula (IX.b) or carboxamide acetals.

If $R^{21}$ is a substituent attached via a hetero atom, the compounds of the formula (XI.2) (iso(thio)ureas, guanidines) can be prepared for example by reacting halogen formamidines of the formula (XII) with alcohols, amines or thiols.

Halogen formamidines of the formula (XII) can be obtained for example by reacting ureas of the formula (XIII) with halogenating agents, for example thionyl chloride (Houben-Weyl-Hagemann, "Methoden der organischen Chemie", 4th edition, volume 4); cf. Scheme 3.

Scheme 3:

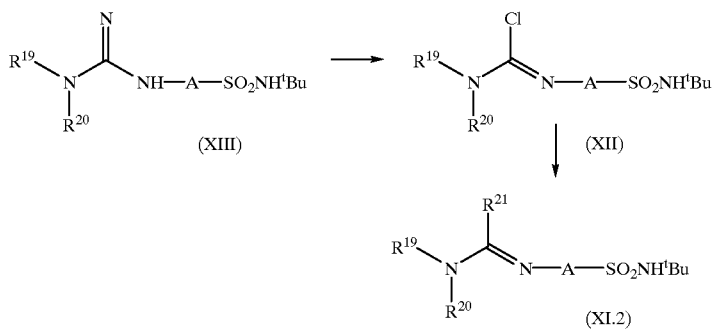

Imino esters of the formula (XI.3) can be obtained for example by reacting ortho esters with anilines of the formula (X) ($R^{18}$=H) (Houben-Weyl-Falbe, "Methoden der organischen Chemie", 4th edition, volume 5/1, p. 812 ff).

Iminocarbonic acid derivatives of the formula (XI.3) ($R^{22}$ is a substituent attached via the hetero atom) can be prepared for example from the corresponding isocyanide dichlorides (=compounds of the formula (XIV)) by successive substitution of the chlorine atoms by alkoxy, amino and alkylmercapto groups. The compounds of the formula (XIV) can be obtained for example from the sulfonamides (X) ($R^{18}$=H) by reaction with thiophosgene and subsequent chlorination (Houben-Weyl-Hagemann, "Methoden der organischen Chemie", 4th edition, volume E4).

Compounds of the formula (XI.4) ($R^{22}$ is hydrogen or a substituent attached via carbon) can be obtained for example by converting anilines of the formula (X) ($R^8$=H) into thiocarboxamides of the formula (XV) and subsequent S-alkylation 30 (Houben-Weyl-Falbe, "Methoden der organischen Chemie", 4th edition, volume E5, p. 931)

(XV)

Imines of the formula (XI.5) can be prepared for example by condensing the aniline (X) ($R^{18}$=H) with aldehydes and ketones or with acetals. (S. Dayagi, Y. Degani in "The Chemistry of the Carbon-Nitrogen Double Bond" (S. Patai (Ed.), p. 61ff, Wiley, London-New York-Sydney-Toronto 1970; R. W. Layer, Chem. Rev. 1963, 489).

Removal of the tert-butyl protecting group from the compounds of the formula (XI) to give the sulfonamides of the formula (II) is carried out by reaction with a strong acid. Suitable acids are for example mineral acids, such as hydrochloric acid and sulfuric acid, or organic acids, for example trifluoroacetic acid or formic acid. The removal of the tert-butyl group is carried out at temperatures from –20° C. to the respective reflux temperature of the reaction mixture, preferably from –10° C. to 60° C. The reaction can be carried out with the neat reactants or in an inert solvent, such as dichloromethane or trichloromethane.

The carbamates needed for the reaction are known from the literature or can be prepared by known methods (cf. EP-A-70804; U.S. Pat. No. 4,480,101; EP-A-562575; EP-A-562576).

The reaction of the compounds of the formula (IV) with heterocyclic amines of the formula (V) is preferably carried out in inert aprotic solvents, for example dioxane, acetonitrile, chlorobenzene or tetrahydrofuran, at temperatures from –10° C. to the boiling point of the solvent.

The sulfonyl isocyanates of the formula (IV) can be prepared by methods known from the literature (e.g. EP-A-184 385) from the sulfonamides of the formula (II). Thus, the reaction of the sulfonamide (II) for example with phosgene in inert solvents, for example dioxane, acetonitrile, chlorobenzene or tetrahydrofuran, at temperatures from 0° C. to the boiling point of the solvent, leads to the compounds of the formula (IV).

The reaction of the sulfonyl chlorides (VI) with the aminoheterocycles of the formula (V) and cyanates such as sodium cyanate and potassium cyanate is carried out for example in aprotic solvents, such as acetonitrile, if appropriate in the presence of bases, for example of 0.5 to 2 equivalents of base, or in basic aprotic solvents at temperatures from –10 to 100° C., preferably –10 to 60° C. Suitable bases or basic aprotic solvents are, for example, pyridine, picoline or lutidine, or a mixture thereof (cf. U.S. Pat. No. 5,157,119).

The reaction of the sulfonamides of the formula (II) with a (thio)isocyanate of the formula (VII) is carried out by methods known from the literature (for example EP-A-232067, EP-A-166516) at from –10 to 150° C., preferably from 20 to 100° C., in an inert solvent, such as acetonitrile, in the presence of a suitable base, such as triethylamine or potassium carbonate.

The reaction of the amino-substituted sulfonylureas of the formula (VIII) or salts thereof with the reagents of the formula (IX) to give sulfonylureas of the formula (I) can be carried out at temperatures of from –20° C. to the boiling point of the respective solvent, preferably from –10° C. to 150° C., in particular from –10° C to 100° C. Suitable solvents are organic solvents, for example ethers, such as tetrahydrofuran, diethyl ether, tert-butyl methyl ether, dimethoxyethane or dioxane, esters, such as ethyl acetate, butyl acetate or methyl acetate, hydrocarbons or halogenated hydrocarbons, such as toluene, xylene, chlorobenzene or chlorotoluene, amides and nitriles, such as dimethylformamide (DMF), N,N-dimethylacetamide, N-methylpyrrolidone, acetonitrile or propionitrile, basic solvents, such as pyridine or lutidine or mixtures of the individual solvents.

The sulfonylureas of the formula (VIII) are known or can be prepared by known methods (for example EP-A-1515, EP-A-23141, U.S. Pat. No. 4,225,337, U.S. Pat. No. 4,310, 346, U.S. Pat. No. 4,453,971, U.S. Pat. No. 4,877,442, U.S. Pat. No. 4,892,946, WO-89/19921).

The reagents of the formula (IX), for example (IXa) and (IXb), are also known from the literature or can be prepared by methods known from the literature (Houben-Weyl-Falbe, "Methoden der organischen Chemie", 4th edition, volume E5, Houben-Weyl-Hagemann, "Methoden der organischen Chemie", 4th edition, volume E4).

The compounds of the general formula (XII), which includes compounds of the formulae (II), (IV), (VI) and (XI), are novel and also form part of the subject matter of this invention:

$$B—A—SO_2—R^Z \quad (XII)$$

Where $R^Z$=$NH_2$, mono- or di-($C_1$–$C_4$-alkyl)amino, halogen or —N=C=O; B and A are as defined in formula (I).

The salts of the compounds of the formula (I) are preferably prepared in inert solvents such as water, methanol, acetone, dichloromethane, tetrahydrofuran, toluene or heptane, at temperatures of 0–100° C. Suitable bases for preparing the salts according to the invention are, for example, alkali metal carbonates, such as potassium carbonate, alkali metal hydroxides and alkaline earth metal hydroxides, for example NaOH, KOH and Ca(OH)$_2$, ammonia or a suitable amine base, such as triethylamine or ethanolamine. Suitable acids for forming salts are, for example, HCl, HBr, H$_2$SO$_4$ or HNO$_3$.

Solvents which have been termed "inert solvents" in the above process variants are to be understood as meaning in each case solvents which are inert under the prevailing reaction conditions, but which do not have to be inert under any selected reaction conditions.

The compounds of the formula (I) and salts thereof according to the invention have an outstanding herbicidal activity against a broad spectrum of economically important monocotyledonous and dicotyledonous harmful plants. The active substances also act efficiently on perennial broadleaved weeds which produce shoots from rhizomes, rootstocks or other perennial organs and which are difficult to control. In this context, it does not matter whether the substances are applied before sowing, pre-emergence or post-emergence. Specifically, examples may be mentioned of some representatives of the monocotyledonous and dicotyledonous weed flora which can be controlled by the compounds according to the invention, without the enumeration being a restriction to certain species.

Examples of weed species on which the active substance acts efficiently are, from amongst the monocotyledons, Avena, Lolium, Alopecurus, Phalaris, Echinochloa, Digitaria, Setaria and also Cyperus species from the annual sector and from amongst the perennial species Agropyron, Cynodon, Imperata and Sorghum, and also perennial Cyperus species.

In the case of the dicotyledonous weed species, the range of action extends to species such as, for example, Galium, Viola, Veronica, Lamium, Stellaria, Amaranthus, Sinapis, Ipomoea, Matricaria, Abutilon and Sida from amongst the annuals, and Convolvulus, Cirsium, Rumex and Artemisia in the case of the perennial weeds.

The active substances according to the invention also effect outstanding control of weeds which occur under the specific conditions of rice growing, such as, for example, Sagittaria, Alisma, Eleocharis, Scirpus and Cyperus.

If the compounds according to the invention are applied to the soil surface before germination, then the weed seedlings are either prevented completely from emerging, or the weeds grow until they have reached the cotyledon stage but then their growth stops, and, eventually, after three to four weeks have elapsed, they die completely.

If the active substances are applied post-emergence to the green parts of the plants, growth likewise stops drastically a very short time after the treatment and the weed plants remain at the growth stage of the point of time of application, or they die completely after a certain time, so that in this manner competition by the weeds, which is harmful to the crop plants, is eliminated at a very early point in time and in a sustained manner.

Even though the compounds according to the invention have an excellent herbicidal activity against monocotyledonous and dicotyledonous weeds, crop plants of economically important crops, such as, for example, wheat, barley, rye, rice, maize, sugar beet, cotton and soya, are damaged not at all, or only to a negligible extent. For these reasons, the present compounds are highly suitable for selectively controlling undesired plant growth in areas under agricultural crops.

In addition, the substances according to the invention have outstanding growth-regulatory properties in crop plants. They engage in the plant metabolism in a regulating manner and can thus be employed for the targeted control of plant constituents and for facilitating harvesting, for example by triggering desiccation and stunted growth. Moreover, they are also suitable for the general control and inhibition of undesirable vegetative growth without destroying the plants in the process. The inhibition of vegetative growth is very important in a large number of monocotyledonous and dicotyledonous crops since it can reduce, or completely prevent, lodging.

The compounds according to the invention can be applied in the form of wettable powders, emulsifiable concentrates, sprayable solutions, dusts or granules in the customary preparations. The invention therefore also relates to herbicidal and plant-growth-regulating compositions which comprise the compounds of the formula (I).

The compounds of the formula (I) can be formulated in various ways, depending on the prevailing biological and/or chemico-physical parameters. The following possibilities are suitable formulations: wettable powders (WP), water-soluble powders (SP), water-soluble concentrates, emulsifiable concentrates (EC), emulsions (EW), such as oil-in-water and water-in-oil emulsions, sprayable solutions, suspension concentrates (SC), oil- or water-based dispersions, solutions which are miscible with oils, capsule suspensions (CS), dusts (DP), seed-dressing products, granules for broadcasting and soil application, granules (GR) in the form of microgranules, spray granules, coated granules and adsorption granules, water-dispersible granules (WG), water-soluble granules (SG), ULV formulations, microcapsules and waxes.

These individual types of formulation are known in principle and are described, for example, in: Winnacker-Küchler, "Chemische Technologie" [Chemical Technology], Volume 7, C. Hauser Verlag Munich, 4th Ed. 1986, Wade van Valkenburg, "Pesticide Formulations", Marcel Dekker, N.Y., 1973; K. Martens, "Spray Drying" Handbook, 3rd Ed. 1979, G. Goodwin Ltd. London.

The formulation auxiliaries required, such as inert materials, surfactants, solvents and other additives are also known and are described, for example, in: Watkins, "Handbook of Insecticide Dust Diluents and Carriers", 2nd Ed., Darland Books, Caldwell N.J., H. v. Olphen, "Introduction to Clay Colloid Chemistry"; 2nd Ed., J. Wiley & Sons, N.Y.; C. Marsden, "Solvents Guide"; 2nd Ed., Interscience, N.Y. 1963; McCutcheon's "Detergents and Emulsifiers Annual", MC Publ. Corp., Ridgewood N.J.; Sisley and Wood, "Encyclopedia of Surface Active Agents", Chem. Publ. Co. Inc., N.Y. 1964; Schönfeldt, "Grenzflächenaktive Äthylenoxidaddukte" [Surface-active ethylene oxide adducts], Wiss. Verlagsgesell., Stuttgart 1976; Winnacker-Küchler, "Chemische Technologie" [Chemical Technology], Volume 7, C. Hauser Verlag Munich, 4th Ed. 1986.

Based on these formulations, it is also possible to prepare combinations with other pesticidally active substances, such as, for example, insecticides, acaricides, herbicides, fungicides, and also with safeners, fertilizers and/or growth regulators, for example in the form of a ready mix or a tank mix.

Wettable powders are preparations which are uniformly dispersible in water and which, besides the active substance, also comprise ionic and/or nonionic surfactants (wetting agents, dispersants), for example polyoxethylated alkylphenols, polyoxethylated fatty alcohols, polyoxethylated fatty amines, fatty alcohol polyglycol ether sulfates, alkanesulfonates, alkylbenzenesulfonates, sodium lignosulfonate, sodium 2,2'-dinaphthylmethane-6,6'-disulfonate, sodium dibutylnaphthalenesulfonate or else sodium oleoylmethyltaurinate, in addition to a diluent or inert substance. To prepare the wettable powders, the herbicidally active substances are ground finely, for example in customary equipment such as hammer mills, blower mills and air-jet mills, and simultaneously or subsequently mixed with the formulation auxiliaries.

Emulsifiable concentrates are prepared, for example, by dissolving the active substance in an organic solvent, for example butanol, cyclohexanone, dimethylformamide, xylene, or else higher-boiling aromatics or hydrocarbons or mixtures of the organic solvents with the addition of one or more ionic and/or nonionic surfactants (emulsifiers). Examples of emulsifiers which can be used are: calcium salts of alkylarylsulfonic acids such as calcium dodecylbenzenesulfonate, or nonionic emulsifiers such as fatty acid polyglycol esters, alkylaryl polyglycol ethers, fatty alcohol polyglycol ethers, propylene oxide/ethylene oxide condensates, alkyl polyethers, sorbitan esters, for example sorbitan fatty acid esters or polyoxyethylene sorbitan esters, for example polyoxyethylene sorbitan fatty acid esters.

Dusts are obtained by grinding the active substance with finely divided solid substances, for example talc, natural clays such as kaolin, bentonite and pyrophyllite, or diatomaceous earth.

Suspension concentrates can be water- or oil-based. They can be prepared, for example, by wet grinding using commercially available bead mills with an optional addition of surfactants as they have already been mentioned above for example in the case of the other types of formulation.

Emulsions, for example oil-in-water emulsions (EW), can be prepared for example by means of stirrers, colloid mills and/or static mixers using aqueous organic solvents and, if appropriate, surfactants as they have already been mentioned above for example in the case of the other types of formulation.

Granules can be prepared either by spraying the active substance onto adsorptive granulated inert material or by applying active substance concentrates to the surface of carriers such as sand, kaolinites or of granulated inert material by means of binders, for example polyvinyl alcohol, sodium polyacrylate or else mineral oils. Suitable active substances can also be granulated in the manner which is conventional for the production of fertilizer granules, if desired as a mixture with fertilizers.

Water-dispersible granules are generally prepared by the customary processes such as spray drying, fluidized-bed granulation, disk granulation, mixing with high-speed mixers and extrusion without solid inert material.

For the preparation of disk, fluidized-bed, extruder and spray granules, see, for example, the processes in "Spray-Drying Handbook" 3rd ed. 1979, G. Goodwin Ltd., London; J. E. Browning, "Agglomeration", Chemical and Engineering 1967, pages 147 et seq.; "Perry's Chemical Engineer's Handbook", 5th Ed., McGraw-Hill, New York 1973, pp. 8–57.

For further details on the formulation of crop protection products see, for example, G. C. Klingman, "Weed Control as a Science", John Wiley and Sons, Inc., New York, 1961, pages 81–96 and J. D. Freyer, S. A. Evans, "Weed Control Handbook", 5th Ed., Blackwell Scientific Publications, Oxford, 1968, pages 101–103.

As a rule, the agrochemical preparations comprise 0.1 to 99% by weight, in particular 0.1 to 95% by weight, of active substance of the formula (I) or of salts thereof.

The active substance concentration in wettable powders is, for example, approximately 10 to 90% by weight, the remainder to 100% by weight being composed of customary formulation components. In the case of emulsifiable concentrates, the active substance concentration may amount to approximately 1 to 90, preferably 5 to 80, % by weight. Formulations in the form of dusts comprise 1 to 30% by weight of active substance, in most cases preferably 5 to 20% by weight of active substance, and sprayable solutions comprise approximately 0.05 to 80, preferably 2 to 50, % by weight of active substance. The active substance content of water-dispersible granules depends partly on whether the active compound is in liquid or solid form and on which granulation auxiliaries, fillers and the like are being used. The active substance content of the water-dispersible granules amounts to, for example, between 1 and 95% by weight, preferably between 10 and 80% by weight.

In addition, the abovementioned formulations of active substances comprise, if appropriate, the adhesives, wetting agents, dispersants, emulsifiers, penetrants, preservatives, antifreeze agents, solvents, fillers, carriers, colorants, antifoams, evaporation inhibitors and pH and viscosity regulators which are customary in each case.

Components which can be used in combination with the active substances according to the invention in mixed formulations or in the tank mix are, for example, known active substances as they are described, for example, in Weed Research 26, 441–445 (1986), or "The Pesticide Manual", 10th edition, The British Crop Protection Council and the Royal Soc. of Chemistry, 1994, and the literature cited therein. Examples of active substances which may be mentioned as herbicides which are known from the literature and which can be combined with the compounds of the formula (I) are the following (note: either the common names in accordance with the International Organization for Standardization (ISO) or the chemical names, if appropriate together with a customary code number, of the compounds are given): acetochlor; acifluorfen; aclonifen; AKH 7088, ie. [[[1-[5-[2-chloro-4-(trifluoromethyl)phenoxy]-2-nitrophenyl]-2-methoxyethylidene]amino]oxy]acetic acid and its methyl ester; alachlor; alloxydim: ametryn: amidosulfuron: amitrol, AMS, ie. ammonium sulfamate; anilofos; asulam; atrazine; azimsulfurone (DPX-A8947); aziprotryn; barban; BAS 516H, ie. 5-fluoro-2-phenyl-4H-3,1-benzoxazin-4-one; benazolin; benfluralin; benfuresate; bensulfuron-methyl; bensulide; bentazone; benzofenap; benzofluor; benzoylprop-ethyl; benzthiazuron; bialaphos; bifenox; bromacil; bromobutide; bromofenoxim; bromoxynil; bromuron; buminafos; busoxinone; butachlor; butamifos; butenachlor; buthidazole; butralin; butylate; cafenstrole (CH-900); carbetamide; cafentrazone (ICI-A0051); CDAA, ie. 2-chloro-N,N-di-2-propenylacetamide; CDEC, ie. 2-chloroallyl diethyldithiocarbamate; chlormethoxyfen; chloramben; chlorazifop-butyl, chlormesulon (ICI-A0051); chlorbromuron; chlorbufam; chlorfenac; chlorflurecol-methyl; chloridazon; chlorimuron-ethyl; chlornitrofen; chlorotoluron; chloroxuron; chlorpropham; chlorsulfuron; chlorthal-dimethyl; chlorthiamid; cinmethylin; cinosulfuron; clethodim; clodinafop and its ester derivatives (for example clodinafop-propargyl); clomazone; clomeprop; cloproxydim; clopyralid; cumyluron (JC 940); cyanazine; cycloate; cyclosulfamuron (AC 104); cycloxydim; cycluron; cyhalofop and its ester derivatives (for example butyl ester, DEH-112); cyperquat; cyprazine; cyprazole; daimuron; 2,4-DB; dalapon; desmedipham; desmetryn; di-allate; dicamba; dichlobenil; dichlorprop; diclofop and its esters, such as diclofop-methyl; diethatyl; difenoxuron; difenzoquat; diflufenican; dimefuron; dimethachlor; dimethametryn; dimethenamid (SAN-582H); dimethazone, clomazon; dimethipin; dimetrasulfuron, dinitramine; dinoseb; dinoterb; diphenamid; dipropetryn; diquat; dithiopyr; diuron; DNOC; eglinazine-ethyl; EL 77, ie. 5-cyano-1-(1,1-dimethylethyl)-N-methyl-1H-pyrazole-4-carboxamide; endothal; EPTC; esprocarb; ethalfluralin; ethametsulfuron-methyl; ethidimuron; ethiozin; ethofumesate; F5231, ie. N-[2-chloro-4-fluoro-5-[4-(3-fluoropropyl)-4,5-dihydro-5-oxo-1H-tetrazol-1-yl]phenyl]ethanesulfonamide; ethoxyfen and its esters (for example ethyl ester, HN-252); etobenzanid (HW 52); fenoprop; fenoxan, fenoxaprop and fenoxaprop-P and their esters, for example fenoxaprop-P-ethyl and fenoxaprop-ethyl; fenoxydim; fenuron; flamprop-methyl; flazasulfuron; fluazifop and fluazifop-P and their esters, for example fluazifop-butyl and fluazifop-P-butyl; fluchloralin; flumetsulam; flumeturon; flumiclorac and its esters (for example pentyl ester, S-23031); flumioxazin (S-482); flumipropyn; flupoxam (KNW-739); fluorodifen; fluoroglycofen-ethyl; flupropacil (UBIC-4243); fluridone; flurochloridone; fluroxypyr; flurtamone; fomesafen; fosamine; furyloxyfen; glufosinate; glyphosate; halosafen; halosulfuron and its esters (for example methyl ester, NC-319); haloxyfop and its esters; haloxyfop-P (=R-haloxyfop) and its esters; hexazinone: imazamethabenzmathyl; imazapyr; imazaquin and salts, such as the ammonium salt; imazethamethapyr; imazethapyr; imazosulfuron; ioxynil; isocarbamid; isopropalin; isoproturon; isouron; isoxaben; isoxapyrifop; karbutilate; lactofen: lenacil: linuron; MCPA; MCPB; mecoprop; mefenacet; mefluidid; metamitron; metazachlor; methabenzthiazuron; metham; methazole; methoxyphenone; methyldymron; metabenzuron, methobenzuron; metobromuron; metolachlor; metosulam (XRD 511); metoxuron; metribuzin; metsulfuron-methyl; MH; molinate; monalide; monocarbamide dihydrogensulfate; monolinuron; monuron; MT 128, ie. 6-chloro-N-(3-chloro-2-propenyl)-5-methyl-N-phenyl-3-pyridazinamine; MT 5950, ie. N-[3-chloro-4-(1-methylethyl)phenyl]-2-methylpentanamide; naproanilide; napropamide; naptalam; NC 310, ie. 4-(2,4-dichlorobenzoyl)-1-methyl-5-benzyloxypyrazole; neburon; nicosulfuron; nipyraclophen; nitralin; nitrofen; nitrofluorfen; norflurazon; orbencarb; oryzalin; oxadiargyl (RP-020630); oxadiazon; oxyfluorfen; paraquat; pebulate; pendimethalin; perfluidone; phenisopham: phenmedipham; picloram; piperophos; piributicarb; pirifenop-butyl; pretilachlor; primisulfuron-methyl; procyazine; prodiamine; profluralin; proglinazine-ethyl; prometon; prometryn; propachlor; propanil; propaquizafop; propazine; propham; propisochlor; propyzamide; prosulfalin; prosulfocarb; prosulfuron (CGA-152005); prynachlor; pyrazolinate; pyrazon; pyrazosulfuron-ethyl; pyrazoxyfen; pyridate; pyrithiobac (KIH-2031); pyroxofop and its esters (for example propargyl ester); quinclorac; quinmerac; quinofop and its ester derivatives, quizalofop and quizalofop-P and their ester derivates, for example quizalofop-ethyl; quizalofop-P-tefuryl and -ethyl; renriduron; rimsulfuron (DPX-E 9636); S 275, ie. 2-[4-chloro-2-fluoro-5-(2-propynyloxy)phenyl]-4,5,6,7-tetrahydro-2H-indazole; secbumeton; sethoxydim; siduron; simazine; simetryn; Ser. No. 106279, ie. 2-[[7-[2-chloro-4-(trifluoromethyl) phenoxy]-2-naphthalenyl]oxy]propanoic acid and its methyl ester; sulfentrazone (FMC-97285, F6285); sulfazuron; sulfometuron-methyl; sulfosate (ICI-A0224); TCA; tebutam (GCP-5544); tebuthiuron; terbacil; terbucarb; terbuchlor; terbumeton; terbuthylazine; terbutryn; TFH 450, ie. N,N-diethyl-3-[(2-ethyl-6-methylphenyl)sulfonyl]-1H-1,2,4-triazole-1-carboxamide; thenylchlor (NSK-850); thiazafluron; thiazopyr (Mon-13200); thidiazimine (SN-24085); thifensulfuron-methyl; thiobencarb; tiocarbazil; tralkoxydim; tri-allate; triasulfuron; triazofenamide; tribenuron-methyl; triclopyr; tridiphane; trietazine; trifluralin; triflusulfuron and esters (for example methyl ester, DPX66037); trimeturon; tsitodef; vernolate; WL 110547, ie. 5-phenoxy-1-[3-(trifluoromethyl)phenyl]-1H-tetrazole; UBH-509; D489; LS 82-556; KPP-300; NC-324; NC-330; KH-218; DPX-N8189; SC-0774: DOWCO-535; DK-8910; V-53482; PP-600; MBH-001; KIH-9201; ET-751; KIH-6127 and KIH-2023.

For use, the formulations, which are in commercially available form, are, if appropriate, diluted in the customary manner, for example using water in the case of wettable powders, emulsifiable concentrates, dispersions and water-dispersible granules. Preparations in the form of dusts, granules for soil application or for broadcasting and sprayable solutions are conventionally not diluted any further with inert substances prior to use.

The application rate required, of the compounds of the formula (I), varies with the external factors such as, inter alia, temperature, humidity and nature of the herbicide used. It can vary within wide limits, for example between 0.001 and 10.0 kg/ha or more of active substance, but it is preferably between 0.005 and 5 kg/ha.

A. CHEMICAL EXAMPLES

Preparation of N-tert-butyl-2-methoxycarbonyl-5-(2-dimethylamino-1-azaethenyl)benzenesulfonamide A mixture of 3.15 g of N-tert-butyl4-amino-2-methoxycarbonylbenzenesulfonamide, 2.2 ml of N,N-dimethylformamide dimethyl acetal and 60 ml of N,N-dimethylformamide is stirred at 50–60° C. until the reaction has ended. The volatile components are then distilled off under reduced pressure. The residue is washed with a little diisopropyl ether. This yields 3.52 g of the desired amidine derivative.

1H-NMR ($D_6$DMSO, 300 MHz) δppm: 7.9 (s, 1H, CH=N); 7.6 (d, 1H); 7.5 (d, 1H); 7.2 (dd, 1H); 6.9 (s, 1H, NH); 9.8 (s, 3H, $OCH_3$); 3.1 (s, 3H, N—$CH_3$); 3.0 (s, 3H, N—$CH_3$); 1.1 (s, 9H, $C(CH_3)_3$).

Preparation of 5-(2-dimethylamino-1-azaethenyl)-2-methoxycarbonyl-benzenesulfonamide A mixture of 2.13 g of N-tert-butyl-2-methoxycarbonyl-5-(2-dimethylamino-1-azaethenyl)benzenesulfonamide and 20 ml of trifluoroacetic acid is stirred at room temperature until the reaction has ended. The volatile components are then distilled off under reduced pressure. The residue is washed with diisopropyl ether and then with NaHCO₃ solution. This affords 1.77 g of the desired compound.

1H-NMR (D₆DMSO, 200 MHz); δppm: 7.9 (s, 1H, CH=N); 7.6 (d, 1H); 7.5 (d, 1H); 7.2 (m, 3H); 3.8 (s, 3H, OCH₃); 3.1 (s, 3H, NCH₃); 3.0 (s, 3H, NCH₃).

Preparation of methyl 2-[[[[(4,6-dimethoxypyrimidin-2-yl)amino]carbonyl]amino]sulfonyl]-4-(2-dimethylamino-1-azaethenyl)-benzoate (cf. Table 2, Ex. No. 2-10)

A suspension of 1.50 g of 5-(2-dimethylamino-1-azaethenyl)-2-methoxycarbonylbenzenesulfonamide, 1.61 g of 4,6-dimethoxy-2-phenoxycarbonylaminopyrimidine, 32 ml of acetonitrile and 0.83 ml of DBU is stirred initially at 0° C. and then at room temperature until the reaction has ended. The reaction mixture is then concentrated under reduced pressure. The residue is taken up in water and washed with diethyl ether. The aqueous phase is carefully acidified with conc. hydrochloric acid (pH 6) and the sulfonylurea precipitate is separated off, washed with diisopropyl ether and water and dried. This affords 1.89 g of the desired sulfonylurea, melting point 73–75° C.;

1H-NMR (D₆-DMSO, 200 MHz); δppm: 12.5 (s,₁H); 10.5 (s, 1H); 8.0 (s, 1H); 7.7 (d, 1H); 7.6 (d, 1H); 7.3 (dd, 1H); 6.0 (s, 1H); 4.0 (s, 6H); 3.8 (s, 3H); 3.1 (s, 3H); 3.0 (s, 3H).

Preparation of the sodium salt of methyl 2-[[[[(4,6-dimethoxypyrimidin-2-yl)amino]carbonyl]amino]sulfonyl]-4-(2-dimethylamino-1-azaethenyl)benzoate (Table 2, Ex. No. 2-46).

0.75 ml of a 30% strength sodium methoxide solution is added dropwise to a mixture of 1.9 g of methyl 2-[[[[(4,6-dimethoxypyrimidin-2-yl)amino]carbonyl]amino]sulfonyl]-4-(2-dimethylamino-1-azaethenyl)-benzoate and 57 ml of dichlorethane. After the reaction has ended, the reaction mixture is intensely concentrated under reduced pressure. This gives 1.95 g of the desired compound with melting point 103–104° C. (decomp.);

1H-NMR (D₆-DMSO, 300 MHz); δppm: 8.6 m, (s, 1H); 7.8 (s, 1H); 7.5 (d, 1H); 7.3 (d, 1H); 7.0 (dd, 1H); 5.7 (s, 1H); 5 3.8 (s, 6H); 3.7 (s, 3H); 3.1 (s, 3H); 3.0 (s, 3H).

Preparation of N,N-dimethyl-2-[[[[(4,6-dimethoxypyrimidin-2-yl)-amino]carbonyl]amino]sulfonyl]-4-(2-dimethylamino-1-azaethenyl)-benzamide (Table 2, Ex. No. 2-15)

0.24 g of (chloromethylene)dimethylammonium chloride is added to a mixture of 0.80 g of N,N-dimethyl-4-amino-2-[[[[(4,6-dimethoxypyrimidin-2-yl)amino]carbonyl]amino]sulfonyl]benzamide and 8 ml of DMF. Stirring is then continued at room temperature until the reaction has ended. Volatile components are then distilled off under reduced pressure. The residue is washed with water and ethyl acetate. After drying, 0.64 g of the desired product is obtained. Melting point: 140–141° C. (decomp.)

Preparation of N-[(4,6-dimethoxypyrimidin-2-yl)aminocarbonyl]-2-(2-dimethylamino-1-azaethenyl)benzenesulfonamide (Table 1, Ex. No. 1-1)

A mixture of 0.80 g of N-[(4,6-dimethoxypyrimidin-2-yl)aminocarbonyl]-2-aminobenzenesulfonamide, 0.29 g of [chloromethylene]dimethylammonium chloride and 8 ml of DMF is stirred at room temperature until the reaction has ended. The volatile components are distilled off under reduced pressure and the residue is washed with water and methyl acetate, affording 0.28 g of the desired product. Melting point: 209–210° C. (decomp.)

The compounds described in the tables below are obtained in a manner similar to the preparation examples above, if appropriate by using the general methods mentioned further above.

The following abbreviations are used in the tables:

No.=Example number mp.=melting point in °C.

Me=methyl

Et=ethyl

Pr=ⁿPr=n-propyl

ⁱPr=i-propyl

ᶜPr=cyclopropyl

ᵗBu=t-butyl

ⁿBu=n-butyl

ᶜBu=cyclobutyl

Ph=phenyl (d)=decomposition

TABLE 1

Compounds of the formula (Ia)

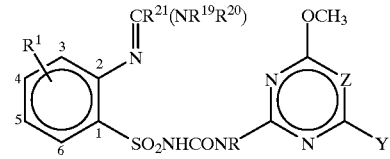

(Ia)

| No. | R¹ | R¹⁹ | R²⁰ | R²¹ | R | Y | Z | mp. |
|---|---|---|---|---|---|---|---|---|
| 1-1 | H | Me | Me | H | H | OMe | CH | 209–210 |
| 1-2 | H | Me | Me | H | H | Cl | CH | |
| 1-3 | H | Me | Me | H | H | OMe | N | |
| 1-4 | H | Me | Me | H | H | Me | N | |
| 1-5 | H | Et | Et | H | H | OMe | CH | 108–109 |
| 1-6 | 6-Cl | Me | Me | H | H | OMe | CH | |
| 1-7 | 6-F | Me | Me | H | H | OMe | CH | |
| 1-8 | 6-OMe | Me | Me | H | H | OMe | CH | |
| 1-9 | H | Me | Me | Me | H | OMe | CH | |
| 1-10 | H | —(CH₂)₄— | | Me | H | OMe | CH | |
| 1-11 | H | —(CH₂)₅— | | Me | H | OMe | CH | |
| 1-12 | H | —(CH₂)₅— | | H | H | OMe | CH | |
| 1-13 | H | —(CH₂)₄— | | H | H | OMe | CH | |
| 1-14 | H | Me | Me | H | H | OMe | CH | Na salt 140–150 |

TABLE 2

Compounds of the formula (Ib)

(Ib)

| No. | R¹ | R¹⁹ | R²⁰ | R²¹ | R | Y | Z | mp. |
|---|---|---|---|---|---|---|---|---|
| 2-1 | H | Me | Me | Me | H | OMe | CH | |
| 2-2 | H | Me | Me | Me | H | Cl | CH | |
| 2-3 | H | Me | Me | Me | H | OMe | N | |
| 2-4 | H | Me | Me | Me | H | Me | N | |
| 2-5 | H | Me | Me | H | H | OMe | CH | |
| 2-6 | 2-Me | Me | Me | H | H | OMe | CH | |
| 2-7 | 2-Cl | Me | Me | H | H | OMe | CH | |
| 2-8 | 2-OMe | Me | Me | H | H | OMe | CH | |
| 2-9 | 2-OEt | Me | Me | H | H | OMe | CH | |
| 2-10 | 2-CO$_2$Me | Me | Me | H | H | OMe | CH | 73–75 |
| 2-11 | 2-CO$_2$Et | Me | Me | H | H | OMe | CH | |
| 2-12 | 2-CO$_2$$^n$Pr | Me | Me | H | H | OMe | CH | |
| 2-13 | 2-CO$_2$-Allyl | Me | Me | H | H | OMe | CH | |
| 2-14 | 2-CO$_2$—$^i$Pr | Me | Me | H | H | OMe | CH | |
| 2-15 | 2-CONMe$_2$ | Me | Me | H | H | OMe | CH | 140–141 |
| 2-16 | 2-CONEt$_2$ | Me | Me | H | H | OMe | CH | |
| 2-17 | 2-CO—N(azetidinyl) | Me | Me | H | H | OMe | CH | |
| 2-18 | 2-CO$_2$—$^c$Bu | Me | Me | H | H | OMe | CH | |
| 2-19 | 2-SEt | Me | Me | H | H | OMe | CH | |
| 2-20 | 2-SMe | Me | Me | H | H | OMe | CH | |
| 2-21 | 2-SO$_2$—Me | Me | Me | H | H | OMe | CH | 181–182 |
| 2-22 | 2-SO$_2$Et | Me | Me | H | H | OMe | CH | 143–145 |
| 2-23 | 2-CO$_2$Me | Me | Me | Me | H | OMe | CH | |
| 2-24 | 2-CO$_2$Me | Me | Me | Et | H | OMe | CH | 186–187 |
| 2-25 | 2-CO$_2$Me | Me | Me | $^n$Pr | H | OMe | CH | |
| 2-26 | 2-CO$_2$Me | Me | Me | $^i$Pr | H | OMe | CH | 93–96 |
| 2-27 | 2-CO$_2$Me | Me | Me | $^c$Pr | H | OMe | CH | |
| 2-28 | 2-CO$_2$Me | Me | Me | $^n$Bu | H | OMe | CH | |
| 2-29 | 2-CO$_2$Me | Me | Me | Allyl | H | OMe | CH | |
| 2-30 | 2-CO$_2$Me | Me | Me | CF$_3$ | H | OMe | CH | |
| 2-31 | 2-CO$_2$Me | Me | Me | Ph | H | OMe | CH | |
| 2-32 | 2-CO$_2$Me | Me | Me | 2-furyl | H | OMe | CH | |
| 2-33 | 2-CO$_2$Me | Me | Me | CH$_3$OCH$_2$ | H | OMe | CH | |
| 2-34 | 2-CO$_2$Me | Me | Me | NMe$_2$ | H | OMe | CH | |
| 2-35 | 2-CO$_2$Me | Me | Me | SMe | H | OMe | CH | |
| 2-36 | 2-CO$_2$Me | —(CH$_2$)$_4$— | | H | H | OMe | CH | 96–98 |
| 2-37 | 2-CO$_2$Me | —(CH$_2$)$_5$— | | H | H | OMe | CH | 148–150 |
| 2-38 | 2-CO$_2$Me | Me | Me | H | Me | OMe | CH | |
| 2-39 | 2-CO$_2$Me | Me | Me | H | H | Cl | CH | 130–132 |
| 2-40 | 2-CO$_2$Me | Me | Me | H | H | OMe | N | |
| 2-41 | 2-CO$_2$Me | Me | Me | H | H | Me | N | 148–149 |
| 2-42 | 2-CO$_2$Me | Me | Me | H | H | CF$_3$ | CH | |
| 2-43 | 2-CO$_2$Me | Me | Me | H | H | CF$_3$ | N | |
| 2-44 | 6-SO$_2$Me | Me | Me | H | H | OMe | CH | |
| 2-45 | 6-SMe | Me | Me | H | H | OMe | CH | |
| 2-46 | 2-COOMe | Me | Me | H | H | OMe | CH | Na salt 103–104 (d) |
| 2-47 | H | Me | Me | H | H | OMe | CH | 156–158 |
| 2-48 | 2-CO$_2$Me | Et | Et | H | H | OMe | CH | 125–128 |
| 2-49 | 2-CO$_2$Me | Et | Et | H | H | OMe | CH | Na salt 173–174 |
| 2-50 | 2-SO$_2$Et | Et | Et | H | H | OMe | CH | 173–175 |
| 2-51 | 2-SO$_2$Me | Me | Me | H | H | Cl | CN | 172–173 |
| 2-52 | 2-SO$_2$Me | Me | Me | H | H | OMe | CH | Na salt 195–198 |

TABLE 2-continued

Compounds of the formula (Ib)

(Ib)

$(R^{19}R^{20}N)R^{21}C=N$-phenyl-$SO_2NHCONR$-pyrimidine with $OCH_3$, Z, Y substituents

| No. | $R^1$ | $R^{19}$ | $R^{20}$ | $R^{21}$ | R | Y | Z | mp. |
|---|---|---|---|---|---|---|---|---|
| 2-53 | 2-CO$_2$Me | Me | Me | Me | H | Me | N | 198–200 |
| 2-54 | 2-SO$_2$Me | Me | Me | Me | H | OMe | CH | 198–199 |
| 2-55 | 2-SO$_2$Me | Me | Me | Et | H | OMe | CH | 199–200 |
| 2-56 | 2-SO$_2$Me | Me | Me | Me | H | OMe | CH | Na salt 218–219 |
| 2-57 | 2-CO$_2$Me | Me | Me | Et | H | OMe | CH | Na salt 170–175 |
| 2-58 | 2-CO$_2$Me | Me | Me | $^i$Pr | H | OMe | CH | Na salt 250–254 |
| 2-59 | 2-CO$_2$Me | —(CH$_2$)$_4$— | | H | H | OMe | CH | Na salt 160–162 |
| 2-60 | 2-CO$_2$Me | —(CH$_2$)$_5$— | | H | H | OMe | CH | Na salt 150–151 |
| 2-61 | 2-CO$_2$Me | Me | Me | H | H | Cl | CH | Na salt 105–108 |
| 2-62 | 2-CO$_2$Me | Me | | —(CH$_2$)$_3$— | H | OMe | CH | 110–115 |
| 2-63 | 2-SO$_2$Et | Me | Me | Me | H | OMe | CH | 185–187 |
| 2-64 | 2-CO$_2$Me | Me | Me | Et | H | Cl | CN | 174–178 |
| 2-65 | 2-CO$_2$Me | —(CH$_2$)$_4$— | | H | H | Cl | CH | 181–183 |
| 2-66 | 2-CO$_2$Me | —(CH$_2$)$_4$— | | H | H | Cl | CH | Na salt 143–146 |
| 2-67 | 2-CO$_2$Me | —(CH$_2$)$_2$—O—(CH$_2$)$_2$— | | Me | H | OMe | CH | 151–154 |
| 2-68 | 2-CO$_2$Me | —(CH$_2$)$_2$—O—(CH$_2$)$_2$— | | H | H | OMe | CH | 96–98 |

TABLE 3

Compounds of the formula (Ic)

(Ic)

| No. | $R^1$ | $R^{19}$ | $R^{20}$ | $R^{21}$ | R | X | Y | Z | mp. |
|---|---|---|---|---|---|---|---|---|---|
| 3-1 | H | H | Me | Me | H | OMe | OMe | CH | |
| 3-2 | H | Me | Me | Me | H | OMe | OMe | CH | |
| 3-3 | 2-CO$_2$Me | H | Me | Me | H | OMe | OMe | CH | |
| 3-4 | 2-CO$_2$Me | Me | Me | Me | H | OMe | OMe | CH | |
| 3-5 | 2-SO$_2$Me | Me | Me | Me | H | OMe | OMe | CH | |
| 3-6 | 2-Cl | H | Me | Me | H | OMe | OMe | CH | |
| 3-7 | 2-OMe | H | Me | Me | H | OMe | OMe | CH | |
| 3-8 | 2-CO$_2$Me | H | Me | Me | H | OMe | Cl | CH | |
| 3-9 | 2-Cl | H | Me | Me | H | OMe | Cl | CH | |
| 3-10 | 2-Cl | H | Me | Me | H | CF$_3$ | OMe | N | |
| 3-11 | 2-Cl | H | Me | Me | H | OMe | OMe | N | |
| 3-12 | 2-NO$_2$ | H | Me | Me | H | OMe | OMe | N | |
| 3-13 | 2-CN | H | Me | Me | H | OMe | OMe | N | |
| 3-14 | 2-NMe$_2$ | H | Me | Me | H | OMe | OMe | N | |

TABLE 4

Compounds of the formula (Id)

(Id)

| No. | $R^1$ | $R^{19}$ | $R^{20}$ | $R^{21}$ | R | mp. |
|---|---|---|---|---|---|---|
| 4-1 | H | Me | Me | H | Me | |
| 4-2 | H | Me | Me | H | H | 135–137 |
| 4-3 | 6-Cl | Me | Me | H | H | |
| 4-4 | 6-F | Me | Me | H | H | |
| 4-5 | 6-CH$_3$ | Me | Me | H | H | |
| 4-6 | 6-CF$_3$ | Me | Me | H | H | |
| 4-7 | H | Et | Et | H | H | |
| 4-8 | H | Et | Me | H | H | |
| 4-9 | H | —(CH$_2$)$_4$— | | H | H | |
| 4-10 | H | —(CH$_2$)$_4$— | | Me | H | |
| 4-11 | H | —(CH$_2$)$_4$— | | Et | H | |
| 4-12 | H | —(CH$_2$)$_5$— | | Et | H | |
| 4-13 | H | —(CH$_2$)$_5$— | | Me | H | |
| 4-14 | H | —(CH$_2$)$_5$— | | H | H | |
| 4-15 | H | Me | Me | CF$_3$ | H | |
| 4-16 | H | Me | Me | SMe | H | |
| 4-17 | H | Me | Me | $^i$Pr | H | 132–136 |
| 4-18 | H | Me | Me | Me | H | 80–90 |
| 4-19 | H | Me | Me | Et | H | 76–80 |

TABLE 5

Compounds of the formula (Ie)

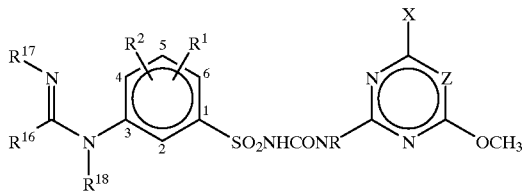

(Ie)

| No. | $R^1$ | $R^2$ | $R^{16}$ | $R^{17}$ | $R^{18}$ | R | X | Z | mp. |
|---|---|---|---|---|---|---|---|---|---|
| 5-1 | H | H | Me | Me | Me | H | OMe | CH | |
| 5-2 | H | H | H | Me | Me | H | OMe | CH | |
| 5-3 | 2-SO$_2$Me | H | Me | Me | Me | H | OMe | CH | |
| 5-4 | 2-SO$_2$Me | H | H | Me | Et | H | OMe | CH | |
| 5-5 | 2-Cl | 6-Cl | H | OH | Me | H | OMe | CH | |
| 5-6 | H | H | H | Me | OMe | H | OMe | CH | |
| 5-7 | 6-CO$_2$Me | H | H | Me | Me | H | OMe | CH | |
| 5-8 | 6-CO$_2$Me | H | Me | Me | Me | H | OMe | CH | |
| 5-9 | 6-CO$_2$Me | H | —(CH$_2$)$_3$— | | Me | H | OMe | CH | |
| 5-10 | 6-CO$_2$Me | H | Me | Me | Me | H | Cl | CH | |
| 5-11 | 6-SO$_2$Me | H | Me | Me | Me | H | Cl | CH | |
| 5-12 | 6-SO$_2$Me | H | Me | Me | Me | H | OMe | CH | |
| 5-13 | 6-SO$_2$Et | H | Me | Me | Me | H | OMe | CH | |
| 5-14 | 6-SO$_2$NMe$_2$ | H | Me | Me | Me | H | OMe | CH | |
| 5-15 | 6-CONMe$_2$ | H | Me | Me | Me | H | OMe | CH | |
| 5-16 | 6-COOMe | H | Ph | SO$_2$Me | Me | H | OMe | CH | |
| 5-17 | 6-COOMe | H | 2-furyl | SO$_2$Me | Me | H | OMe | CH | |
| 5-18 | H | H | H | CO$_2$Me | Me | H | OMe | CH | |
| 5-19 | H | H | H | COCH$_3$ | Me | H | OMe | CH | |
| 5-20 | H | H | OMe | Me | Me | H | OMe | CH | |

TABLE 6

Compounds of the formula (If)

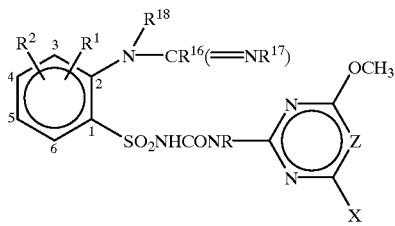

(If)

| No. | $R^1$ | $R^2$ | $R^{16}$ | $R^{17}$ | $R^{18}$ | R | X | Z | mp. |
|---|---|---|---|---|---|---|---|---|---|
| 6-1 | H | H | H | Me | Me | H | OMe | CH | |
| 6-2 | H | H | H | Ph | Me | H | OMe | CH | |
| 6-3 | H | H | H | CO—Ph | Me | H | OMe | CH | |
| 6-4 | H | H | H | CO—Me | Me | H | OMe | CH | |
| 6-5 | H | H | H | COCF$_3$ | Me | H | OMe | CH | |
| 6-6 | H | H | H | SO$_2$Me | Me | H | OMe | CH | |
| 6-7 | H | H | H | SO$_2$Ph | Me | H | OMe | CH | |
| 6-8 | H | H | H | Me | OMe | H | OMe | CH | |
| 6-9 | H | H | H | Me | Et | H | OMe | CH | |
| 6-10 | 6-CO$_2$Me | H | H | Me | Me | H | OMe | CH | |
| 6-11 | 6-SO$_2$Me | H | H | Me | Me | H | OMe | CH | |
| 6-12 | 6-Cl | H | H | Me | Me | H | OMe | CH | |
| 6-13 | 4-Cl | 6-Cl | H | Me | Me | H | OMe | CH | |
| 6-14 | 4-Me | 6-Me | H | Me | Me | H | OMe | CH | |
| 6-15 | H | H | CF$_3$ | Me | Me | H | OMe | CH | |

TABLE 6-continued

Compounds of the formula (If)

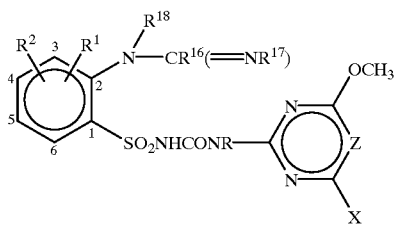

(If)

| No. | R¹ | R² | R¹⁶ | R¹⁷ | R¹⁸ | R | X | Z | mp. |
|---|---|---|---|---|---|---|---|---|---|
| 6-16 | H | H | Ph | Me | Me | H | OMe | CH | |
| 6-17 | H | H | 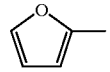 (furan) | Me | Me | H | OMe | CH | |
| 6-18 | H | H | 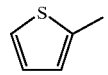 (thiophene) | Me | Me | H | OMe | CH | |
| 6-19 | H | H |  (pyridine) | Me | Me | H | OMe | CH | |
| 6-20 | H | H | ᵗBu | Me | Me | H | OMe | CH | |

TABLE 7

Compounds of the formula (Ig)

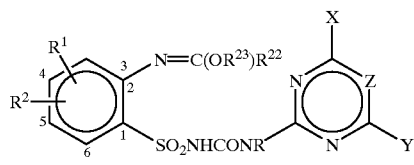

(Ig)

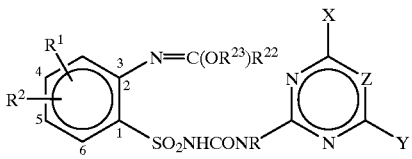

(Ig)

| No. | R¹ | R² | R²² | R²³ | R | X | Y | Z | mp. |
|---|---|---|---|---|---|---|---|---|---|
| 7-1 | H | H | H | Me | H | OMe | OMe | CH | |
| 7-2 | H | H | CF₃ | Me | H | OMe | OMe | CH | |
| 7-3 | H | H | H | Et | H | OMe | OMe | CH | |
| 7-4 | 6-OMe | H | Ph | Me | H | OMe | OMe | CH | |
| 7-5 | H | H |  (furan) | Me | H | OMe | OMe | CH | |
| 7-6 | H | H | 3,6-C₆H₃Cl₂— | Me | H | OMe | OMe | CH | |
| 7-7 | H | H | (thiophene) | Me | H | OMe | OMe | CH | |
| 7-8 | 6-Me | H | Me | Me | H | OMe | OMe | CH | |
| 7-9 | 6-OEt | H | Me | Me | H | OMe | OMe | CH | |
| 7-10 | H | H | CH₃OCH₂ | Me | H | OMe | OMe | CH | |

TABLE 8

Compounds of the formula (Ih)

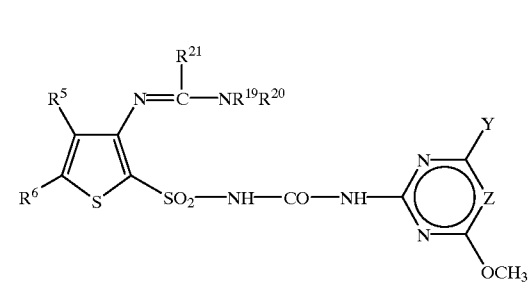

(Ih)

| No. | R¹ | R² | R²² | R²³ | R | Y | Z | mp. |
|---|---|---|---|---|---|---|---|---|
| 8-1 | H | H | H | Me | H | OMe | CH | |
| 8-2 | H | H | Ph | Me | H | OMe | CH | |
| 8-3 | 2-Cl | H | H | Me | H | OMe | CH | |
| 8-4 | 2-OMe | H | H | Me | H | OMe | CH | |
| 8-5 | 2-OEt | H | H | Me | H | OMe | CH | |
| 8-6 | 2-CF₃ | H | H | Me | H | OMe | CH | |
| 8-7 | 6-CF₃ | H | H | Me | H | OMe | CH | |
| 8-8 | 6-CO₂Me | H | H | Me | H | OMe | CH | |
| 8-9 | 6-SMe | H | H | Me | H | OMe | CH | |
| 8-10 | 6-SCH₂CF₃ | H | H | Me | H | OMe | CH | |
| 8-11 | 6-SO₂CH₂F | H | H | Me | H | OMe | CH | |
| 8-12 | 6-CH₂CH₂CF₃ | H | H | Me | H | OMe | CH | |
| 8-13 | 4-Cl | 6-Cl | H | Me | H | OMe | CH | |
| 8-14 | 4-F | 6-F | H | Me | H | OMe | CH | |
| 8-15 | 4-F | 6-CO₂Me | H | Me | H | OMe | CH | |
| 8-16 | H | H | CF₃ | Et | H | OMe | CH | |
| 8-17 | H | H | 2-furyl | Allyl | H | OMe | CH | |

TABLE 9

Compounds of the formula (Ik)

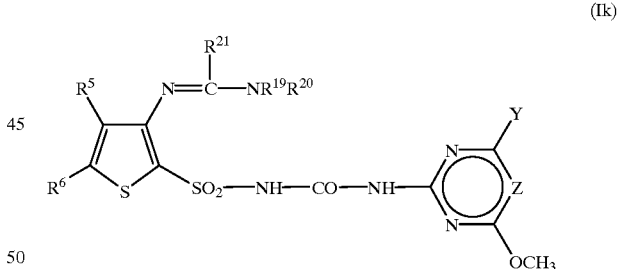

(Ik)

| No. | R⁵ | R⁶ | R¹⁹ | R²⁰ | R²¹ | Y | Z | mp. |
|---|---|---|---|---|---|---|---|---|
| 9-1 | H | H | Me | Me | Me | OMe | CH | 97–101 |
| 9-2 | H | H | Me | Me | Me | OMe | CH | Na salt 95 (d.) |
| 9-3 | H | H | Me | Me | ⁱPr | OMe | CH | 130 (d.) |
| 9-4 | H | H | Me | Me | ⁱPr | OMe | CH | Na salt 175–177 (d.) |
| 9-5 | H | H | Me | Me | H | OMe | CH | 107–110 (d.) |
| 9-6 | H | H | Me | Me | H | OMe | CH | Na salt 147–149 (d.) |
| 9-7 | Me | H | Me | Me | Me | OMe | CH | |
| 9-8 | H | Me | Me | Me | Me | OMe | CH | |
| 9-9 | Me | Me | Me | Me | Me | OMe | CH | |
| 9-10 | H | H | Me | Me | Me | Cl | CH | |
| 9-11 | H | H | Me | Me | ⁱPr | Cl | CH | |
| 9-12 | H | H | Me | Me | Me | Me | N | |
| 9-13 | H | H | Me | Me | ⁱPr | Me | N | |
| 9-14 | Me | H | Me | Me | Me | Me | N | |
| 9-15 | H | Me | Me | Me | Me | Me | N | |
| 9-16 | Me | Me | Me | Me | Me | Me | N | |

TABLE 10

Compounds of the formula (Im)

$$\text{(Im)}$$

Structure: $R^{14}$ on pyrazole ring with $N=C(R^{21})-NR^{19}R^{20}$ substituent, $SO_2-NH-CO-NH$- linker to pyrimidine ring with Y, Z, and $OCH_3$ substituents; $R^{15}$ on pyrazole N.

| No. | $R^{14}$ | $R^{15}$ | $R^{19}$ | $R^{20}$ | $R^{21}$ | Y | Z | mp. |
|---|---|---|---|---|---|---|---|---|
| 10-1 | Me | Me | Me | Me | H | OMe | CH | 122–125 (d.) |
| 10-2 | Me | Me | Me | Me | H | OMe | CH | Na salt 122–126 (d.) |
| 10-3 | H | Me | Me | Me | H | OMe | CH | |
| 10-4 | H | H | Me | Me | H | OMe | CH | |
| 10-5 | H | H | Me | Me | Me | OMe | CH | |
| 10-6 | Me | Me | Me | Me | Me | OMe | CH | |
| 10-7 | Me | H | Me | Me | H | OMe | CH | |
| 10-8 | Me | Me | Me | Me | H | Cl | CH | |
| 10-9 | H | Me | Me | Me | H | Cl | CH | |
| 10-10 | H | H | Me | Me | H | Cl | CH | |
| 10-11 | H | H | Me | Me | H | Cl | CH | |
| 10-12 | Me | Me | Me | Me | H | Me | N | |
| 10-13 | H | Me | Me | Me | H | Me | N | |
| 10-14 | H | H | Me | Me | H | Me | N | |
| 10-15 | H | H | Me | Me | Me | Me | N | |
| 10-16 | Me | Me | Me | Me | Me | Me | N | |

B. FORMULATION EXAMPLES a) A dust is obtained by mixing 10 parts by weight of a compound of the formula (I) and 90 parts by weight of talc as inert substance and comminuting the mixture in a hammer mill.

b) A wettable power which is readily dispersible in water is obtained by mixing 25 parts by weight of a compound of the formula (I), 64 parts by weight of kaolin-containing quartz as inert substance, 10 parts by weight of potassium lignosulfonate and 1 part by weight of sodium oleoylmethyltaurate as wetting agent and dispersant, and grinding the mixture in a pinned-disk mill.

c) A dispersion concentrate which is readily dispersible in water is obtained by mixing 20 parts by weight of a compound of the formula (I) with 6 parts by weight of alkylphenyl polyglycol ether (®Triton X 207), 3 parts by weight of isotridecanol polyglycol ether (8 EO) and 71 parts by weight of paraffinic mineral oil (boiling range for example approx. 255 to above 277° C.), and grinding the mixture in a ball mill to a fineness of below 5 microns.

d) An emulsifiable concentrate is obtained from 15 parts by weight of a compound of the formula (I), 75 parts by weight of cyclohexanone as solvent and 10 parts by weight of oxethylated nonylphenol as emulsifier.

e) Granules which are dispersible in water are obtained by mixing 75 parts by weight of a compound of the formula (I),
10 parts by weight of calcium lignosulfonate,
5 parts by weight of of sodium lauryl sulfate,
3 parts by weight of polyvinyl alcohol and
7 parts by weight of kaolin, grinding the mixture on a pinned-disk mill and granulating the powder in a fluidized bed by spraying on water as granulation liquid.

f) Water-dispersible granules are also obtained by homogenizing, on a colloid mill, 25 parts by weight of a compound of the formula (I),
5 parts by weight of sodium 2,2'-dinaphthylmethane-6,6'-disulfonate,
2 parts by weight of sodium oleoylmethyltaurate,
1 part by weight of polyvinyl alcohol,
17 parts by weight of calcium carbonate and
50 parts by weight of water, precomminuting the mixture, subsequently grinding it on a bead mill and atomizing and drying the resulting suspension in a spray tower by means of a single-substance nozzle.

C. BIOLOGICAL EXAMPLES

1. Pre-emergence Effect on Weeds

Seeds or rhizome pieces of monocotyledonous and dicotyledonous weed plants are placed in sandy loam soil in plastic pots and covered with soil. The compounds of the formula (I) or salts thereof according to the invention which have been formulated in the form of wettable powders or emulsion concentrates are then applied to the surface of the soil cover in the form of aqueous suspensions or emulsions at an application rate of 600 to 500 l of water/ha (converted), in various dosages.

After the treatment, the pots are placed in a greenhouse and kept under good growth conditions for the weeds. After the test plants have emerged after a period of 3 to 4 weeks, the damage to the plants or the negative effect on the emergence is scored visually by comparison with untreated controls. As shown by the test results, the compounds according to the invention have a good herbicidal pre-emergence activity against a broad spectrum of grass weeds and broad-leaved weeds. For example, the compounds of Preparation Examples Nos. 1-1, 1-5, 1-14, 2-10, 2-15, 2-21, 2-22, 2-24, 2-26, 2-36, 2-37, 2-39, 2-41, 2-47, 2-48, 2-49, 2-50, 2-51 to 4-2, 4-17, 4-18, 4-19, 9-1, 9-2, 9-3, 9-4, 9-5, 9-6, 10-1 and 10-2 (see Section A.) show a very good herbicidal activity in the test against harmful plants such as Sinapis alba, Stellaria media, Chrysanthemum segetum, and Lolium multiflorum when applied pre-emergence at a rate of application of 0.3 kg to 0.005 kg of active ingredient per hectare.

2. Post-emergence Effect on Weeds

Seeds or rhizome pieces of monocotyledonous and dicotyledonous weeds are placed in sandy loam soil in plastic pots, covered with soil and grown in a greenhouse under good growth conditions. Three weeks after sowing, the test plants are treated in the three-leaf stage. The compounds of the formula (I) or salts thereof according to the invention which have been formulated as wettable powders or as emulsion concentrates are sprayed in various dosages onto the green parts of the plants at an application rate of 600 to 800 l of water/ha (converted). After the test plants have remained in the greenhouse for about 3 to 4 weeks under ideal growth conditions, the effect of the preparations is scored visually by comparison with untreated controls. The agents according to the invention also have a good herbicidal post-emergence activity against a broad range of economically important grass weeds and broad-leaved weeds. For example, Preparation Examples Nos. 1-1, 1-5, 1-14, 2-10, 2-15, 2-21, 2-22, 2-24, 2-26, 2-36, 2-37, 2-39, 2-41, 2-47, 2-48 2-49, 2-50, 2-51 to 2-68, 4-2, 4-17, 4-18, 4-19, 9-1, 9-2, 9-3, 9-4, 9-5, 9-6, 10-1 and 10-2 (see Section A.) show a very good herbicidal activity in the test against harmful plants such as Sinapis alba, Stellaria media, Chrysanthemum segetum, and Lolium multiflorum when applied post-emergence at an application rate of 0.3 kg to 0.005 kg of active ingredient per hectare.

3. Tolerance by Crop Plants

In further greenhouse experiments, seeds of a substantial number of crop plants and weeds were placed in sandy loam substrate and covered with soil.

Some of the pots were treated immediately as described in Section 1, and the remaining pots were placed in a greenhouse until the plants had developed two to three true leaves and then sprayed with various dosages of the substances of the formula (I) or salts thereof according to the invention as described in Section 2.

Visual scoring four to five weeks after application and after the plants had remained in the greenhouse revealed that the compounds according to the invention did not inflict any damage to dicotyledonous crops such as soy beans, cotton, oil seed rape, sugar beet and potatoes when used pre- and post-emergence, even when high dosages of active substance were used. Moreover, some substances also left Gramineae crops such as barley, wheat, rye, Sorghum species, maize or rice unharmed. The compounds of the formula (I) or salts thereof therefore have a high selectivity when used for controlling undesirable vegetation in agricultural crops.

What is claimed is:

1. A compound of the formula (I) or a salt thereof

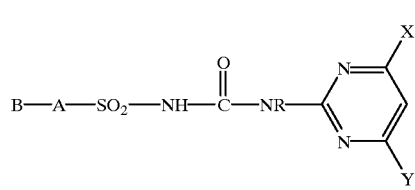

(I)

wherein

A is a bridge of the formulae $A_1$–$A_9$

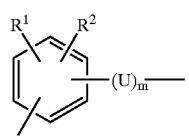

A1

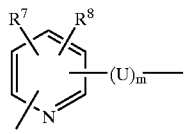 A2

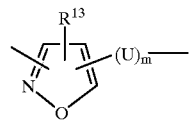 A3

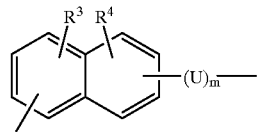 A4

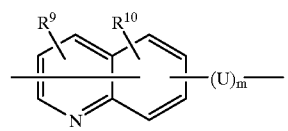 A5

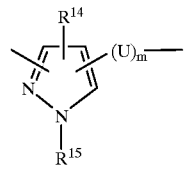 A6

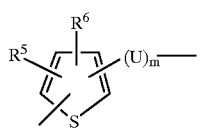 A7

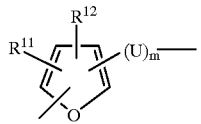 A8

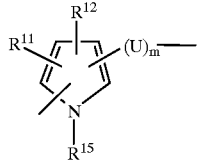 A9 m is 0 or 1,

U is $CH_2$, O or NH or $(C_1$–$C_3$-alkyl)N,

B is a group of the formula B1 to B5,

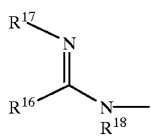 B1

-continued

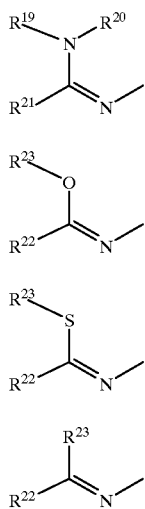

R is hydrogen, $C_1$–$C_5$-alkyl, $C_1$–$C_5$-haloalkyl, $C_2$–$C_5$-alkenyl, $C_2$–$C_5$-haloalkenyl, $C_2$–$C_5$-alkynyl or $C_2$–$C_5$-haloalkynyl, $R^1$ is H, CN, halogen, azide, $NO_2$, OH, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_1$–$C_8$-alkylsulfinyl, $C_2$–$C_8$-alkenylsulfinyl, $C_2$–$C_8$-alkynylsulfinyl, $C_1$–$C_8$-alkylsulfonyl, $C_2$–$C_8$-alkenylsulfonyl, $C_2$–$C_8$-alkynylsulfonyl, $C_3$–$C_8$-cycloalkyl, $C_3$–$C_8$-cycloalkyloxy, $C_3$–$C_8$-cycloalkylthio, $C_3$–$C_8$-cycloalkylsulfinyl, $C_3$–$C_8$-cycloalkylsulfonyl, $C_5$–$C_8$-cycloalkenyl, $C_5$–$C_8$-cycloalkenyloxy, $C_5$–$C_8$-cycloalkenylthio, $C_5$–$C_8$-cycloalkenylsulfinyl or $C_5$–$C_8$-cycloalkenylsulfonyl, each of the last 25 radicals being unsubstituted or substituted by one or more radicals from the group consisting of halogen, $C_1$–$C_4$-alkoxy, $C_1$–$C_4$-haloalkoxy, $C_1$–$C_4$-alkylthio, $C_1$–$C_4$-haloalkylthio, OH, CN, $NO_2$, oxo, $C_1$–$C_4$-alkylsulfonyl, $C_{1-C4}$-haloalkylsulfonyl, ($C_1$–$C_4$-alkoxy)carbonyl, ($C_1$–$C_4$-haloalkoxy)-carbonyl, $NR^{32}R^{33}$ and, in the case of cyclic radicals, also $C_1$–$C_4$-alkyl and $C_1$–$C_4$-haloalkyl, or is $COR^{24}$, $CSR^{25}$, $C(=Nk^{26})R^{27}$, $NR^{28}R^{29}$, $SO_2NR^{30}R^{31}$ or a heterocycle which is unsubstituted or substituted by one or more radicals from the group consisting of halogen, $C_1$–$C_4$-alkyl, OH, CN, $NO_2$, CHO, $NH_2$, mono- and di-($C_1$–$C_4$-alkyl)amino, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylcarbonyl, $C_1$–$C_4$-alkoxycarbonyl and oxo, or is aryl, hetaryl, aryl-$C_1$–$C_3$-alkyl or hetaryl-$C_1$–$C_3$-alkyl, the aryl or hetaryl moiety of each of the last 4 radicals being unsubstituted or substituted by one or more radicals from the group consisting of halogen, OH, CN, nitro, $C_1$–$C_4$-alkyl, $C_1$–$C_4$-haloalkyl, $C_1$–$C_4$-alkoxy, $C_1$–$C_4$-haloalkoxy, $C_1$–$C_4$-alkylthio, $C_1$–$C_4$-haloalkylthio, $C_1$–$C_4$-alkylsulfonyl, $C_1$–$C_4$-haloalkylsulfonyl, $C_1$–$C_4$-alkylcarbonyl, $C_1$–$C_4$-haloalkylcarbonyl, ($C_1$–$C_4$-alkoxy)carbonyl, ($C_1$–$C_4$-haloalkoxy)-carbonyl, mono- and di($C_1$–$C_4$-alkyl)amino, CHO, $NH_2$, $CONH_2$, mono- and di-($C_1$–$C_4$-alkyl)-aminocarbonyl, $R^2$ is hydrogen, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_1$–$C_8$-alkylsulfonyl, $C_2$–$C_8$-alkenylsulfonyl, $C_2$–$C_8$-alkynylsulfonyl, $C_3$–$C_8$-cycloalkyl, $C_5$–$C_8$-cycloalkenyl, $C_5$–$C_8$-cycloalkoxy, $C_5$–$C_8$-cycloalkenyloxy, $C_3$–$C_8$-cycloalkylthio, $C_5$–$C_8$-cycloalkenylthio, $C_3$–$C_8$-cycloalkylsulfonyl or $C_5$–$C_8$-cycloalkenylsulfonyl, each of the last 20 radicals being unsubstituted or substituted by one or more radicals from the group consisting of halogen, $C_1$–$C_4$-alkoxy and $C_1$–$C_4$-haloalkoxy and, in the case of cyclic radicals, also $C_1$–$C_4$-alkyl and $C_1$–$C_4$-haloalkyl, or is halogen, CN, $NH_2$, mono- or di-($C_1$–$C_4$-alkyl)amino, $R^3$, $R^5$, $R^7$, $R^9$, $R^{11}$, $R^{13}$, and $R^{14}$ are each a radical from the group of the radicals as defined for $R^1$, $R^4$, $R^6$, $R^8$, $R^{10}$ and $R^{12}$ are each a radical from the group of the radicals as defined for $R^2$, $R^{15}$ is hydrogen, $C_1$–$C_8$-alkyl, $C_3$–$C_8$-cycloalkyl, $C_1$–$C_8$-haloalkyl, $C_3$–$C_8$-halocycloalkyl, or aryl which is unsubstituted or substituted by one or more radicals from the group consisting of halogen, $C_1$–$C_4$-alkyl, $C_1$–$C_4$-haloalkyl; $C_1$–$C_4$-alkoxy and $C_1$–$C_4$-haloalkoxy, $R^{16}$ is $NH_2$, hydrogen, aryl or hetaryl, each of the last two radicals being unsubstituted or substituted, or $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, $C_3$–$C_8$-cycloalkyl, $C_5$–$C_8$-cycloalkenyl, $C_3$–$C_6$-cycloalkoxy, $C_5$–$C_8$-cycloalkenyloxy, $C_3$–$C_8$-cycloalkylthio, $C_5$–$C_8$-cycloalkenylthio, mono-or di-($C_1$–$C_6$)alkylamino, each of the last 17 radicals being unsubstituted or substituted, or benzyl, CN, ($C_1$–$C_6$-alkoxy)carbonyl, ($C_1$–$C_6$-alkyl)carbonyl, benzyloxycarbonyl or phenylcarbonyl, $R^{17}$ is OH, $NH_2$, hydrogen, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, ($C_1$–$C_8$-alkyl)carbonyl, ($C_1$–$C_8$-alkoxy)carbonyl, benzoyl, benzyloxycarbonyl, ($C_1$–$C_8$)-alkylsulfonyl, arylsulfonyl, $C_3$–$C_8$-cycloalkyl, $C_5$–$C_8$-cycloalkenyl, $C_3$–$C_8$-cycloalkoxy, $C_5$–$C_8$-cycloalkenyloxy, $C_3$–$C_8$-cycloalkylcarbonyl, $C_3$–$C_8$-cycloalkoxycarbonyl, $C_3$–$C_8$-cyclo-alkylsulfonyl, mono- or di-($C_1$–$C_8$-alkyl)amino, each of the last 21 radicals being unsubstituted or substituted by one or more radicals from the group consisting of halogen, $C_1$–$C_4$-alkoxy, $C_1$–$C_4$-haloalkoxy, CN, $NO_2$, OH, $NH_2$, mono- and di-($C_1$–$C_3$-alkyl)amino, $C_1$–$C_4$-alkylthio and $C_1$–$C_4$-haloalkylthio and, in the case of cyclic radicals, also $C_1$–$C_4$-alkyl and $C_1$–$C_4$-haloalkyl, or is aryl or hetaryl, each of the last 2 radicals being unsubstituted or substituted by one or more radicals from the group consisting of $C_1$–$C_4$-alkyl, $C_1$–$C_4$-haloalkyl, $C_1$–$C_4$-alkoxy, $C_1$–$C_4$-haloalkoxy, CN and $NO_2$, or the part of the formula

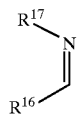

from the group of the abovementioned formula B1 (see definition of B) as a whole forms a heterocyclic ring having an imino function, wherein said rings are selected from a ring of the formulae D1 to D15

D1 

D2 

D3 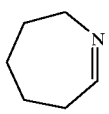

D4 

D5 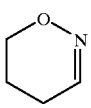

D6 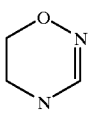

D7 

D8 

D9 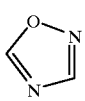

D10 

D11 

D12 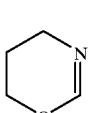

D13 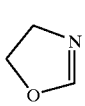

D14 

D15 

wherein said rings D1 to D15 are unsubstituted or substituted by one or more radicals from the group consisting of halogen, $C_1$–$C_4$-alkyl, $C_1$–$C_4$-haloalkyl, $C_1$–$C_4$-haloalkoxy, OH, $NH_2$, CN, $NO_2$, mono- and di-($C_1$–$C_4$-alkyl)amino.

$R^{18}$ is hydrogen, $C_{1-C_8}$-alkyl, $C_2$–$C_8$-alkenyl, $C_2$–$C_8$-alkynyl, $C_1$–$C_8$-alkylsulfonyl, ($C_1$–$C_8$-alkyl)carbonyl, ($C_1$–$C_8$-alkoxy)carbonyl, $C_{1-5}$-alkoxy, $C_3$–$C_8$-cycloalkyl, $C_5$–$C_8$-cycloalkenyl, $C_3$–$C_8$-cycloalkylsulfonyl, $C_3$–$C_8$-cycloalkylcarbonyl, $C_3$–$C_8$-cycloalkoxycarbonyl or $C_3$–$C_8$-cycloalkoxy, each of the last 13 radicals being unsubstituted or substituted by one or more radicals from the group consisting of halogen, $C_1$–$C_3$-alkoxy, $C_1$–$C_3$-haloalkoxy and, in the case of cyclic radicals, also $C_1$–$C_4$-alkyl and $C_1$–$C_4$-haloalkyl, or is CHO, $NH_2$, OH, mono- or di-($C_1$–$C_4$-alkyl)amino, $R^{19}$ is a radical selected from the group of the radicals as defined for $R^{17}$ and $R^{20}$ is hydrogen, $C_1$–$C_8$-alkyl, $C_3$–$C_8$-cycloalkyl, $C_2$–$C_8$-alkenyl, $C_3$–$C_8$-cycloalkenyl or $C_2$–$C_6$-alkynyl or $NR^{19}R^{20}$ is a heterocyclic ring, having 3 to 6 ring atoms and, in addition to the 1-nitrogen atom, may optionally contain one further hetero ring atom selected from the group consisting of N, O, and S which is unsubstituted or substituted by one or more radicals from the group consisting of halogen, $C_1$–$C_4$-alkyl, $C_1$–$C_4$-haloalkyl, $C_1$–$C_4$-alkoxy, $C_1$–$C_4$-haloalkoxy, OH, $NH_2$, $NO_2$, CN, mono- and di-($C_1$–$C_5$-alkyl)amino, $R^{21}$ is a radical from the group of the radicals possible for $R^{16}$, $R^{22}$ is hydrogen, $C_1$–$C_8$-alkyl, $C_2$–$C_8$-alkenyl, $C_2$–$C_8$-alkynyl, $C_1$–$C_8$-alkoxy, $C_1$–$C_8$-alkylthio, $C_3$–$C_8$-cycloalkoxy, $C_3$–$C_8$-cycloalkylthio, $C_3$–$C_8$-cycloalkyl, $C_5$–$C_8$-cycloalkenyl, mono- or di-($C_1$–$C_8$-alkyl)amino, each of the last 11 radicals being unsubstituted or substituted by one or more radicals from the group consisting of CN, halogen, $C_1$–$C_4$-alkoxy, $C_1$–$C_4$-haloalkoxy and, in the case of cyclic radicals, also $C_1$–$C_4$-alkyl and $C_1$–$C_4$-haloalkyl, or is aryl or hetaryl, $R^{23}$ is $C_1$–$C_8$-alkyl, $C_2$–$C_8$-alkenyl, $C_2$–$C_8$-alkynyl, $C_3$–$C_8$-cycloalkyl, $C_5$–$C_8$-cycloalkenyl, heterocyclyl, aryl or benzyl, each of the last 8 radicals being unsubstituted or substituted by one or more radicals from the group consisting of halogen, $C_1$–$C_4$-alkoxy, $C_1$–$C_4$-haloalkoxy, CN and $NO_2$ and, in the case of cyclic radicals, also $C_1$–$C_4$-alkyl and $C_1$–$C_4$-haloalkyl, $R^{24}$ is hydrogen, OH, $NH_2$, aryl or a heterocycle, each of the last two radicals being unsubstituted or substituted, or is $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylthio, $C_2$–$C_8$-alkenylthio, $C_2$–$C_8$-alkynylthio, benzyl, aryloxy, benzyloxy, $C_3$–$C_8$-cycloalkyl, $C_5$–$C_8$-cycloalkenyl, $C_3$–$C_8$-cycloalkoxy, $C_5$–$C_8$-cycloalkenyloxy, $C_5$–$C_8$-cycloalkylthio or $C_5$–$C_8$-cycloalkenylthio, mono- or di-($C_1$–$C_8$-alkyl) amino, each of the last 20 radicals being unsubstituted or substituted by one or more radicals from the group consisting of halogen, $C_1$–$C_4$-alkoxy, $C_1$–$C_4$-haloalkoxy, OH, $NH_2$, mono- and di-($C_1$–$C_4$-alkyl) amino, CN and $NO_2$ and, in the case of cyclic radicals, also $C_1$–$C_4$-alkyl and $C_1$–$C_4$-haloalkyl, $R^{25}$ is a radical from the group of the radicals possible for $R^{24}$, $R^{26}$ is hydrogen, OH, $NH_2$, CN, $C_1$–$C_8$-alkoxy, $C_2$–$C_8$-alkenyloxy, $C_2$–$C_8$-alkynyloxy, $C_1$–$C_8$-alkyl, $C_2$–$C_8$-alkenyl, $C_2$–$C_8$-alkynyl, $C_1$–$C_8$-alkylsulfonyl, $C_2$–$C_8$-alkenylsulfonyl, $C_2$–$C_8$-alkynylsulfonyl, $C_3$–$C_8$-cycloalkoxy, $C_5$–$C_8$-cycloalkenyloxy, $C_3$–$C_8$-cycloalkyl, $C_5$–$C_8$-cycloalkenyl, $C_3$–$C_8$-cycloalkylsulfonyl, $C_5$–$C_8$-cycloalkenylsulfonyl, arylsulfonyl or aryl or a heterocycle or benzyl, ($C_1$–$C_8$-alkoxy)carbonyl, ($C_1$–$C_8$-alkyl)carbonyl, phenoxycarbonyl, benzylcarbonyl or heterocyclylcarbonyl, each of the last 24 radicals being unsubstituted or substituted, $R^{27}$ is a radical from the group of the radicals possible for $R^{24}$, excluding OH, $R^{28}$ is H, OH, CHO, $C_1$–$C_8$-alkyl, $C_2$–$C_8$-alkenyl, $C_2$–$C_8$-alkynyl, $C_1$–$C_8$-alkoxy, $C_2$–$C_8$-alkenyloxy, $C_2$–$C_8$-alkynyloxy, $C_1$–$C_8$-alkylsulfonyl, $C_2$–$C_8$-alkenylsulfonyl, $C_2$–$C_8$-alkynylsulfonyl, ($C_1$–$C_8$-alkyl)carbonyl, ($C_2$–$C_8$-alkenyl)carbonyl, ($C_2$–$C_8$-alkynyl)carbonyl, ($C_1$–$C_8$-alkoxy)carbonyl, ($C_2$–$C_8$-alkenyloxy)carbonyl, ($C_2$–$C_8$-alkynyloxy)carbonyl, mono- or di-($C_1$–$C_8$-alkyl)-aminocarbonyl, $C_3$–$C_8$-cycloalkyl, $C_5$–$C_8$-cycloalkenyl, $C_3$–$C_8$-cycloalkoxy, $C_5$–$C_8$-cycloalkenyloxy, $C_3$–$C_9$-cycloalkylsulfonyl, $C_5$–$C_8$-cycloalkenylsulfonyl, $C_3$–$C_8$-cycloalkoxycarbonyl, $C_5$–$C_8$-cycloalkenyloxycarbonyl, benzoyl, benzyl, benzylcarbonyl, benzyloxycarbonyl, aryl or a heterocycle, each of the last 31 radicals being unsubstituted or substituted, or is $SO_2NH_2$ or $CONH_2$, $R^{29}$ is a radical from the group of the radicals possible for $R^{28}$, excluding OH, $R^{30}$ is a radical from the group of the radicals possible for $R^{19}$, $R^{31}$ is a radical from the group of the radicals possible for $R^{20}$, or $NR^{30}R^{31}$ as a whole forms a heterocyclic ring as defined for $NR^{19}R^{20}$, $R^{32}$ is hydrogen, $C_1$–$C_4$-alkyl, $C_1$–$C_4$-haloalkyl, CHO, $C_1$–$C_4$-alkylsulfonyl, $C_2$–$C_4$-alkenyl, $C_2$–$C_4$-alkynyl, $C_2$–$C_4$-haloalkenyl, $C_1$–$C_4$-haloalkyl, $C_2$–$C_4$-haloalkynyl, $C_1$–$C_4$-haloalkylsulfonyl, ($C_1$–$C_4$-alkyl)carbonyl, ($C_1$–$C_4$-alkoxy)carbonyl, ($C_1$–$C_4$-haloalkyl) carbonyl or ($C_1$–$C_4$-haloalkoxy)carbonyl, $R^{33}$ is a radical from the group of the radicals possible for $R^{32}$ or $NR^{32}R^{33}$ as a whole forms a heterocyclic ring as defined for $NR^{19}R^{20}$. and wherein, unless otherwise defined, aryl is a mono-, bi- or polyaromatic ring system which has 6 to 12 carbon atoms which is substituted or unsubstituted, hetaryl is a mono-, bi- or polyaromatic ring system which has 6 to 12 carbon atoms wherein one of said carbon atoms is replaced by a heteroatom selected from the group consisting of N, O, and sulfur or is heteroring selected from the group consisting of pyrimidine, pyridazine, pyrazine, thiazole, oxazole, pyrazole, imidazole, quinoline, and benzoxazole which are substituted or unsubstituted; heterocyclyl or heterocyclic ring is saturated, unsaturated or aromatic ring containing 3 to 8 carbon atoms wherein one of the carbon atoms is replaced by a hetero atom selected from the group consisting of N, O, and S, or is a heteroring selected from the group consisting of piperdine, piperazine, dioxolane, morpholine, pyrimidine, pyridazine, thiazole, oxazole, pyrazole, imidazole, quinoline, and benzoxazole, which are substituted or unsubstituted; and said substituents on the aryl, hetaryl, heterocyclyl or heterocyclic ring are one or more radicals selected from the group consisting of halogen, $C_1$–$C_4$-alkyl, $C_2$–$C_4$-alkenyl, $C_2$–$C_4$-alkenyl, aryl, heterocyclyl, $C_1$–$C_4$-haloalkyl, $C_1$–$C_4$-alkoxy, $C_1$–$C_4$-haloalkoxy, OH, NH, $NH_2$, $NO_2$, CN, N≡N, $C_1$–$C_4$-alkylthio, $C_1$–$C_4$-alkoxycarbonyl, $C_1$–$C_4$-alkylcarbonyl, formyl, carbamoyl, mono-($C_1$–$C_4$)-alkylamino, di-($C_1$–$C_4$)-alkylamino, mono-($C_1$–$C_4$)alkylamino carbonyl, di($C_1$–$C_4$-alkyl)carbonyl, acylamino, $C_1$–$C_4$-alkylsulfinyl, halo-($C_1$–$C_4$)-alkylsulfinyl, $C_1$–$C_4$-alkylsulfonyl, halo($C_1$–$C_4$-alkyl)sulfonyl, $C_2$–$C_4$-alkenyloxy, and $C_2$–$C_4$-alkynyloxy.

2. A compound of the formula (I) or a salt thereof as claimed in claim 1, wherein R is hydrogen, $C_2$–$C_3$-alkyl, $C_1$–$C_3$-alkoxy, $R^1$ is H, CN, $NO_2$, halogen, $C_1$–$C_6$-alkoxy, $C_1$–$C_6$-alkyl, $C_1$–$C_6$-haloalkoxy, $C_1$–$C_6$-haloalkyl, ($C_1$–$C_6$-alkoxy) carbonyl, ($C_3$–$C_6$-cycloalkoxy)carbonyl or ($C_3$–$C_6$-cycloalkyl)methoxycarbonyl, ($C_3$–$C_6$-cycloalkoxy) carbonyl, ($C_3$–$C_6$-cycloalkyl)-methoxycarbonyl, $C_1$–$C_6$-alkylthio, $C_1$–$C_6$-haloalkylthio, $C_1$–$C_6$-alkylsulfonyl, $C_1$–$C_6$-haloalkylsulfonyl, $SO_2NH_2$, $CONH_2$, mono- or di-($C_1$–$C_4$-alkyl)aminocarbonyl or -aminosulfonyl or a radical of the formula

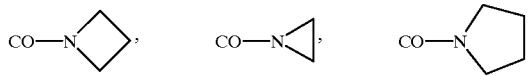

or $C_1$–$C_6$-alkylcarbonyl, $C_1$–$C_6$-haloalkylcarbonyl, CHO, cyclopropylcarbonyl, cyclobutylcarbonyl or $NR^{28}R^{29}$;

$R^2$ is hydrogen, $C_{1-C6}$-alkyl, $C_1$–$C_6$-haloalkyl, $C_1$–$C_6$-alkoxy, $C_1$–$C_6$-haloalkoxy, halogen or CN;

$R^3$, $R^5$, $R^7$, $R^9$, $R^{11}$, $R^{13}$ and $R^{14}$ are each a radical from the group of radicals possible for $R^1$, $R^4$, $R^6$, $R^8$, $R^{10}$, $R^{12}$ are each a radical from the group of radicals possible for $R^2$, $R^{15}$ is H, $C_1$–$C_3$-alkyl or phenyl;

$R^{16}$ is H, $NH_2$, mono- or di-($C_1$–$C_6$-alkyl)amino, $C_1$–$C_6$-alkyl, phenyl, $C_1$–$C_6$-alkoxy, each of the last 5 radicals being unsubstituted or substituted by one or more radicals from the group consisting of halogen, $C_1$–$C_3$-alkoxy, $C_1$–$C_3$-haloalkoxy, CN, $NO_2$ and, in the case of phenyl, also $C_1$–$C_3$-alkyl and $C_1$–$C_3$-haloalkyl;

$R^{17}$ is H, OH, $NH_2$, mono- or di-($C_1$–$C_6$-alkyl)amino, $C_1$–$C_6$-alkyl, $C_1$–$C_6$-alkoxy, phenyl, benzyl, each of the last 6 radicals being unsubstituted or substituted by one or more radicals from the group consisting of halogen, $C_1$–$C_3$-alkoxy, $C_1$–$C_3$-haloalkoxy and, in the case of phenyl, also $C_1$–$C_3$-alkyl and $C_1$–$C_3$-haloalkyl, or the part of the formula R$^{17}$—N=C—R$^{16}$ from the group of the formula B1

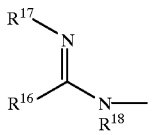

in the definition for B as a whole forms a heterocycle of the formula D1 or D2

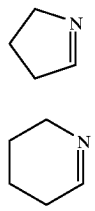

R$^{18}$ is H, C$_1$–C$_6$-alkyl or C$_1$–C$_6$-haloalkyl,

R$^{19}$ is H, C$_1$–C$_6$-alkyl, C$_1$–C$_6$-haloalkyl, C$_1$–C$_6$-haloalkoxy or phenyl, R$^{20}$ is H, C$_1$–C$_6$-alkyl, C$_1$–C$_6$-haloalkyl or phenyl or NR$^{19}$R$^{20}$ as a whole forms a heterocycle of the formula

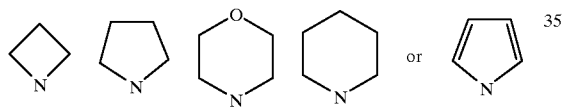

R$^{21}$ is a radical from the group of radicals possible for R$^{16}$;

R$^{22}$ is H, C$_1$–C$_6$-alkyl, C$_1$–C$_6$-haloalkyl or phenyl;

R$^{23}$ is C$_1$–C$_6$-alkyl or C$_1$–C$_6$-haloalkyl;

R$^{28}$ is H, C$_1$–C$_6$-alkyl, OH, C$_1$–C$_6$-haloalkyl, or C$_1$–C$_6$-alkoxy, R$^{29}$ is H, C$_1$–C$_6$-alkyl, C$_1$–C$_6$-haloalkyl, CHO, C$_1$–C$_3$-alkylsulfonyl, C$_1$–C$_3$-alkoxycarbonyl or C$_1$–C$_3$-alkylcarbonyl;

X and Y are each independently of the other Cl, F, CF$_3$, CH$_3$, CH$_2$CH$_3$, OCH$_3$, OC$_2$H$_5$, N(CH$_3$)$_2$, NHCH$_3$ or OCH$_2$CF$_3$.

3. The compound of the formula (I) or a salt thereof according to claim 1 wherein A is

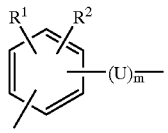

4. The compound of the formula (I) or a salt thereof according to claim 3, wherein B is

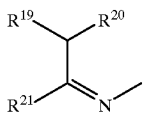

5. The compound or a salt thereof according to claim 4, wherein

R is H or C$_1$–C$_4$-alkyl;

R$^1$ is H, CN, NO$_2$, halogen, C$_1$–C$_6$-alkoxy, C$_1$–C$_6$-alkyl, C$_1$–C$_6$-haloalkoxy, C$_1$–C$_6$-haloalkyl, (C$_1$–C$_6$-alkoxy)carbonyl, (C$_3$–C$_6$-cycloalkoxy)carbonyl or (C$_3$–C$_6$-cycloalkyl)methoxycarbonyl, (C$_3$–C$_6$-cycloalkoxy)carbonyl, (C$_3$–C$_6$-cycloalkyl)-methoxycarbonyl, C$_1$–C$_6$-alkylthio, C$_1$–C$_6$-haloalkylthio, C$_1$–C$_6$-alkylsulfonyl, C$_1$–C$_6$-haloalkylsulfonyl, SO$_2$NH$_2$, CONH$_2$, mono- or di-(C$_1$–C$_4$-alkyl)aminocarbonyl or -aminosulfonyl, C$_1$–C$_6$-alkylcarbonyl, C$_1$–C$_6$-haloalkylcarbonyl, CHO, cyclopropylcarbonyl, cyclobutylcarbonyl or NR$^{28}$R$^{29}$;

R$^2$ is hydrogen, C$_1$–C$_6$-alkyl, C$_1$–C$_6$-haloalkyl, C$_1$–C$_6$-alkoxy, C$_1$–C$_6$-haloalkoxy, halogen or CN;

m is 0;

R$^{19}$ is H, C$_1$–C$_6$-alkyl, or C$_1$–C$_6$-haloalkyl, C$_1$–C$_6$-haloalkoxy or phenyl;

R$^{20}$ is H, C$_1$–C$_6$-alkyl, C$_1$–C$_6$-haloalkyl, or phenyl;

R$^{21}$ is H, NH$_2$, mono- or di-(C$_1$–C$_6$-alkyl)amino, C$_1$–C$_6$-alkyl, phenyl, C$_1$–C$_6$-alkoxy, each of the last 5 radicals being unsubstituted or substituted by one or more radicals from the group consisting of halogen, C$_1$–C$_3$-alkoxy, C$_1$–C$_3$-haloalkoxy, CN, NO$_2$ and, in the case of phenyl, also C$_1$–C$_3$-alkyl and C$_1$–C$_3$-haloalkyl;

R$^{22}$ is H, C$_1$–C$_6$-alkyl, C$_1$–C$_6$-haloalkyl or phenyl;

R$^{23}$ is C$_1$–C$_6$-alkyl or C$_1$–C$_6$-haloalkyl;

R$^{28}$ is H, C$_1$–C$_6$-alkyl, OH, C$_1$–C$_6$-haloalkyl, or C$_1$–C$_6$-alkoxy;

R$^{29}$ is H, C$_1$–C$_6$-alkyl, C$_1$–C$_6$-haloalkyl, CHO, C$_1$–C$_3$-alkylsulfonyl; C$_1$–C$_3$-alkoxycarbonyl or C$_1$–C$_3$-alkylcarbonyl;

X and Y are each independently of the other Cl, F, CF$_3$, CH$_3$, CH$_2$CH$_3$, OCH$_3$, OC$_2$H$_5$, N(CH$_3$)$_2$, NHCH$_3$ or OCH$_2$CF$_3$.

6. The compound according to claim 4 which has the formula

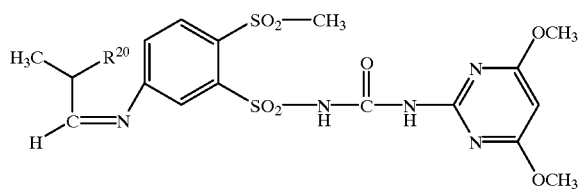

or

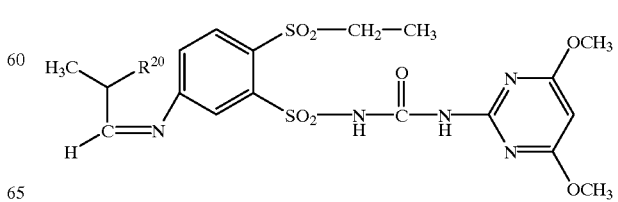

7. A herbicidal or plant growth regulating composition, which comprises one or more compounds of the formula (I) or a salt thereof as claimed in claim 1 and formulation auxiliaries customary in crop protection.

8. A method for controlling harmful plants or for regulating the growth of plants, which comprises applying an active amount of one or more compounds of the formula (I) or a salt thereof as claimed in claim 1 to the plants, seeds thereof or the area where they grow.

* * * * *

UNITED STATES PATENT AND TRADEMARK OFFICE
CERTIFICATE OF CORRECTION

PATENT NO. : 6,410,482 B1
DATED : June 25, 2002
INVENTOR(S) : Schnabel et al.

It is certified that error appears in the above-identified patent and that said Letters Patent is hereby corrected as shown below:

<u>Column 48,</u>
Line 26, before the period ".", insert the following:

--one of the radicals X and Y is halogen, $C_1$-$C_6$-alkyl, $C_1$-$C_6$-alkoxy, $C_1$-$C_6$-alkylthio, the last 3 radicals being unsubstituted or substituted by one or more radicals from the group consisting of halogen, $C_1$-$C_4$-alkoxy and $C_1$-$C_4$-alkylthio, or is $C_2$-$C_4$-alkenyl, $C_2$-$C_4$-alkynyl, $C_2$-$C_4$-alkenyloxy or $C_2$-$C_4$-alkynyloxy, each of the last 4 radicals being unsubstituted or substituted by one or more halogen atoms, or is $C_3$-$C_6$-cycloalkyl or mono-or-di-($C_1$-$C_2$-alkyl)amino and the other of the radicals X and Y is halogen, $C_1$-$C_4$-alkyl, $C_1$-$C_4$-alkoxy or $C_1$-$C_4$-alkylthio, each of the last 3 radicals being unsubstituted or substituted by one or more radicals from the group consisting of halogen, $C_1$-$C_4$-alkoxy and $C_1$-$C_4$-alkylthio, or is mono-or-di-($C_1$-$C_2$-alkyl)amino--

Signed and Sealed this

Nineteenth Day of August, 2003

JAMES E. ROGAN
*Director of the United States Patent and Trademark Office*